United States Patent
Kowalewski et al.

(10) Patent No.: US 10,646,118 B2
(45) Date of Patent: May 12, 2020

(54) LASER CATHETER WITH USE OF REFLECTED LIGHT TO DETERMINE MATERIAL TYPE IN VASCULAR SYSTEM

(71) Applicant: Regents of the University of Minnesota, Minneapolis, MN (US)

(72) Inventors: Timothy M. Kowalewski, Saint Paul, MN (US); Darrin D. Beekman, Minneapolis, MN (US); Jack B. Stubbs, Lake Elmo, MN (US); Paul Anthony Iaizzo, White Bear Lake, MN (US); Gregory K. Peterson, Saint Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 14 days.

(21) Appl. No.: 14/586,312

(22) Filed: Dec. 30, 2014

(65) Prior Publication Data

US 2016/0183804 A1    Jun. 30, 2016

(51) Int. Cl.
*A61B 5/00* (2006.01)
*A61B 18/24* (2006.01)
(Continued)

(52) U.S. Cl.
CPC .......... *A61B 5/0084* (2013.01); *A61B 5/4887* (2013.01); *A61B 18/245* (2013.01);
(Continued)

(58) Field of Classification Search
CPC ................ A61B 5/0084; A61B 18/245; A61B 2018/00345; A61B 2018/00577; A61B 2018/00785; A61B 5/1076; A61B 5/4887
(Continued)

(56) References Cited

U.S. PATENT DOCUMENTS 4,053,845 A    10/1977  Gould
4,641,912 A     2/1987  Goldenberg
(Continued)

FOREIGN PATENT DOCUMENTS

EP    0211984 B2    3/1987
EP    2319404 B1    5/2011
(Continued)

OTHER PUBLICATIONS

Darrin D. Beekman. Tissue Identification and Photoablation Therapy Control with Contact Diffuse Reflectance Spectroscopy. PhD thesis, The University of Minnesota Twin Cities, 2018. (Year: 2018).*

(Continued)

*Primary Examiner* — Gary Jackson
*Assistant Examiner* — Jonathan Kuo

(57) ABSTRACT

Apparatus and methods for determining a type of a material in a region within a vascular system of a patient and/or a distance to the material are provided. At least one source fiber is provided that supplies light from a light source to a region within a vascular system of a patient. At least one return fiber is provided to receive light reflected from the region within the vascular system. At least one controller is provided to determine at least one property of the region within the vascular system from the reflected light, and to determine a type of a material in the region within the vascular system and/or an indication of a distance to the material. Techniques such as laser ablation may then be performed based on the determined material type and/or distance to remove unwanted buildup, deposits, etc., while avoiding harmful results such as tearing of tissue.

17 Claims, 14 Drawing Sheets

(51) Int. Cl.
  *A61B 5/02* (2006.01)
  *A61B 18/00* (2006.01)
  *A61B 5/107* (2006.01)
(52) U.S. Cl.
  CPC ......... *A61B 5/02007* (2013.01); *A61B 5/1076* (2013.01); *A61B 5/7282* (2013.01); *A61B 2018/00345* (2013.01); *A61B 2018/00577* (2013.01); *A61B 2018/00785* (2013.01)
(58) Field of Classification Search
  USPC ............... 600/407, 425, 427, 476–480, 483; 607/88
  See application file for complete search history.

(56) References Cited

U.S. PATENT DOCUMENTS

| | | |
|---|---|---|
| 4,669,465 A | 6/1987 | Moore et al. |
| 4,686,979 A | 8/1987 | Gruen et al. |
| 4,732,448 A | 3/1988 | Goldenberg |
| 4,747,405 A | 5/1988 | Leckrone |
| 4,769,005 A | 9/1988 | Ginsburg et al. |
| 4,784,132 A | 11/1988 | Fox et al. |
| 4,788,975 A | 12/1988 | Shturman et al. |
| 4,799,754 A | 1/1989 | Goldenberg |
| 4,807,620 A | 2/1989 | Strul et al. |
| 4,830,460 A | 5/1989 | Goldenberg |
| 4,844,062 A | 7/1989 | Wells |
| 4,848,336 A | 7/1989 | Fox et al. |
| 4,850,686 A | 7/1989 | Morimoto et al. |
| 4,913,142 A | 4/1990 | Kittrell et al. |
| 4,919,508 A | 4/1990 | Grace et al. |
| 4,924,863 A | 5/1990 | Sterzer |
| 4,925,265 A | 5/1990 | Rink et al. |
| 5,016,964 A | 5/1991 | Donnelly |
| 5,024,234 A | 6/1991 | Leary et al. |
| 5,026,366 A | 6/1991 | Leckrone |
| 5,029,588 A | 7/1991 | Yock et al. |
| 5,034,010 A | 7/1991 | Kittrell et al. |
| 5,040,548 A | 8/1991 | Yock |
| 5,041,108 A | 8/1991 | Fox et al. |
| 5,047,952 A | 9/1991 | Kramer et al. |
| 5,154,680 A * | 10/1992 | Drzewiecki ........ A61B 5/02416 600/485 |
| 5,165,897 A | 11/1992 | Johnson |
| 5,176,674 A | 1/1993 | Hofmann |
| 5,188,632 A | 2/1993 | Goldenberg |
| 5,207,672 A | 5/1993 | Roth et al. |
| 5,217,454 A | 6/1993 | Khoury |
| 5,243,546 A * | 9/1993 | Maggard ................... G01J 3/28 702/90 |
| 5,250,045 A | 10/1993 | Bohley |
| 5,263,953 A | 11/1993 | Bagby |
| 5,267,341 A | 11/1993 | Shearin |
| 5,300,085 A | 4/1994 | Yock |
| 5,304,171 A | 4/1994 | Gregory et al. |
| 5,318,032 A | 6/1994 | Lonsbury et al. |
| 5,350,375 A | 9/1994 | Deckelbaum et al. |
| 5,350,377 A | 9/1994 | Winston et al. |
| 5,350,395 A | 9/1994 | Yock |
| 5,352,197 A | 10/1994 | Hammersmark et al. |
| 5,377,683 A | 1/1995 | Barken |
| 5,395,361 A | 3/1995 | Fox et al. |
| 5,400,428 A | 3/1995 | Grace |
| 5,415,653 A | 5/1995 | Wardle et al. |
| 5,423,740 A | 6/1995 | Sullivan et al. |
| 5,425,355 A | 6/1995 | Kulick |
| 5,427,920 A * | 6/1995 | Berndt .................. G01N 21/253 356/339 |
| 5,429,604 A | 7/1995 | Hammersmark et al. |
| 5,429,617 A | 7/1995 | Hammersmark et al. |
| 5,440,664 A | 8/1995 | Harrington et al. |
| 5,451,233 A | 9/1995 | Yock |
| 5,456,680 A | 10/1995 | Taylor et al. |
| 5,464,395 A | 11/1995 | Faxon et al. |
| 5,470,330 A | 11/1995 | Goldenberg et al. |
| 5,483,080 A * | 1/1996 | Tam ........................ G01N 21/51 250/574 |
| 5,484,433 A | 1/1996 | Taylor et al. |
| 5,492,131 A | 2/1996 | Galel |
| 5,514,128 A | 5/1996 | Hillsman et al. |
| 5,536,242 A | 7/1996 | Willard et al. |
| 5,571,151 A | 11/1996 | Gregory |
| 5,573,531 A | 11/1996 | Gregory |
| 5,623,940 A | 4/1997 | Daikuzono |
| 5,643,251 A | 7/1997 | Hillsman et al. |
| 5,649,923 A | 7/1997 | Gregory et al. |
| 5,657,760 A | 8/1997 | Ying et al. |
| 5,713,894 A | 2/1998 | Murphy-Chutorian et al. |
| 5,722,972 A | 3/1998 | Power et al. |
| 5,755,714 A | 5/1998 | Murphy-Chutorian |
| 5,792,118 A | 8/1998 | Kurth et al. |
| 5,800,350 A | 9/1998 | Coppleson et al. |
| 5,803,083 A | 9/1998 | Buck et al. |
| 5,807,377 A | 9/1998 | Madhani et al. |
| 5,817,144 A | 10/1998 | Gregory |
| 5,824,005 A | 10/1998 | Motamedi et al. |
| 5,824,026 A | 10/1998 | Diaz |
| 5,830,209 A | 11/1998 | Savage et al. |
| 5,836,946 A | 11/1998 | Diaz et al. |
| RE36,104 E | 2/1999 | Solar |
| 5,891,133 A | 4/1999 | Murphy-Chutorian |
| 5,938,602 A | 8/1999 | Lloyd |
| 5,938,609 A | 8/1999 | Pomeranz |
| 5,976,124 A | 11/1999 | Reiser |
| 5,986,643 A | 11/1999 | Harvill et al. |
| 5,989,243 A | 11/1999 | Goldenberg |
| 6,022,342 A | 2/2000 | Mukherjee |
| 6,033,402 A | 3/2000 | Tu et al. |
| 6,036,715 A | 3/2000 | Yock |
| 6,056,743 A | 5/2000 | Ellis et al. |
| 6,066,130 A | 5/2000 | Gregory et al. |
| 6,117,128 A | 9/2000 | Gregory |
| 6,231,563 B1 | 5/2001 | White et al. |
| 6,251,104 B1 | 6/2001 | Kesten et al. |
| 6,287,297 B1 | 9/2001 | Woodruff et al. |
| 6,290,668 B1 | 9/2001 | Gregory et al. |
| 6,302,875 B1 | 10/2001 | Makower et al. |
| 6,370,411 B1 | 4/2002 | Osadchy et al. |
| 6,419,684 B1 | 7/2002 | Heisler et al. |
| 6,432,115 B1 | 8/2002 | Mollenauer et al. |
| 6,447,504 B1 | 9/2002 | Ben-Haim et al. |
| 6,447,525 B2 | 9/2002 | Follmer et al. |
| 6,458,098 B1 | 10/2002 | Kanesaka |
| 6,539,132 B2 | 3/2003 | Ivtsenkov et al. |
| 6,571,118 B1 * | 5/2003 | Utzinger ............... A61B 5/0071 356/318 |
| 6,575,993 B1 | 6/2003 | Yock |
| 6,597,829 B2 | 7/2003 | Cormack |
| 6,733,495 B1 | 5/2004 | Bek et al. |
| 6,743,208 B1 | 6/2004 | Coyle |
| 6,792,390 B1 | 9/2004 | Burnside et al. |
| 6,842,639 B1 * | 1/2005 | Winston ............... A61B 5/0084 356/477 |
| 7,238,178 B2 | 7/2007 | Maschke |
| 7,319,566 B2 | 1/2008 | Prince et al. |
| 7,568,619 B2 | 8/2009 | Todd et al. |
| 7,572,254 B2 | 8/2009 | Hebert et al. |
| 7,846,153 B2 | 12/2010 | Hebert et al. |
| 7,930,065 B2 | 4/2011 | Larkin et al. |
| 7,959,608 B2 | 6/2011 | Nash et al. |
| 7,988,633 B2 | 8/2011 | Hossack et al. |
| 8,016,745 B2 | 9/2011 | Hassler et al. |
| 8,016,748 B2 | 9/2011 | Mourlas et al. |
| 8,050,739 B2 | 11/2011 | Eck et al. |
| 8,100,893 B2 | 1/2012 | Dadisman |
| 8,361,097 B2 | 1/2013 | Patel et al. |
| 8,545,488 B2 | 10/2013 | Taylor et al. |
| 8,628,519 B2 | 1/2014 | Taylor et al. |
| 2001/0014805 A1 | 8/2001 | Burbank et al. |
| 2002/0013572 A1 | 1/2002 | Berlin |
| 2002/0026118 A1 | 2/2002 | Govari |
| 2002/0045811 A1 | 4/2002 | Kittrell et al. |
| 2002/0072661 A1 | 6/2002 | Wiesmann et al. |

(56) References Cited

U.S. PATENT DOCUMENTS

| | | |
|---|---|---|
| 2002/0103459 A1 | 8/2002 | Sparks et al. |
| 2002/0107445 A1 | 8/2002 | Govari |
| 2002/0159685 A1 | 10/2002 | Cormack |
| 2003/0032936 A1 | 2/2003 | Lederman |
| 2003/0045798 A1 | 3/2003 | Hular et al. |
| 2003/0078566 A1 | 4/2003 | Elliott et al. |
| 2003/0204185 A1 | 10/2003 | Sherman et al. |
| 2003/0219202 A1 | 11/2003 | Loeb et al. |
| 2004/0010204 A1 | 1/2004 | Weber et al. |
| 2004/0057659 A1 | 3/2004 | Baugh |
| 2004/0059280 A1 | 3/2004 | Makower et al. |
| 2004/0075919 A1 | 4/2004 | Diaz et al. |
| 2004/0111016 A1* | 6/2004 | Casscells, III ........... A61B 5/01 600/310 |
| 2004/0127889 A1 | 7/2004 | Zhang et al. |
| 2004/0133154 A1 | 7/2004 | Flaherty et al. |
| 2004/0162548 A1 | 8/2004 | Reiser |
| 2005/0004453 A1* | 1/2005 | Tearney ............... A61B 5/0066 600/427 |
| 2005/0149176 A1 | 7/2005 | Heggestuen et al. |
| 2005/0203416 A1 | 9/2005 | Angelsen et al. |
| 2006/0020260 A1 | 1/2006 | Dover et al. |
| 2006/0094930 A1 | 5/2006 | Sparks et al. |
| 2006/0173359 A1* | 8/2006 | Lin ...................... A61B 5/4244 600/478 |
| 2006/0217695 A1 | 9/2006 | DeBenedictis et al. |
| 2006/0247532 A1* | 11/2006 | Ramanujam ......... A61B 5/0091 600/476 |
| 2007/0060879 A1 | 3/2007 | Weitzner et al. |
| 2007/0106289 A1 | 5/2007 | O'Sullivan |
| 2007/0115152 A1 | 5/2007 | Bjorklund et al. |
| 2008/0019657 A1 | 1/2008 | Maitland et al. |
| 2008/0058629 A1* | 3/2008 | Seibel .................. A61B 1/0008 600/368 |
| 2008/0106388 A1 | 5/2008 | Knight |
| 2008/0108867 A1 | 5/2008 | Zhou |
| 2008/0154296 A1* | 6/2008 | Taylor ...................... A61B 1/32 606/190 |
| 2009/0177095 A1 | 7/2009 | Aeby et al. |
| 2009/0203989 A1 | 8/2009 | Burnside et al. |
| 2010/0114081 A1 | 5/2010 | Keeler et al. |
| 2010/0152717 A1 | 6/2010 | Keeler |
| 2010/0168569 A1 | 7/2010 | Sliwa et al. |
| 2010/0177309 A1* | 7/2010 | Scaiano ..................... G01J 3/02 356/319 |
| 2010/0200076 A1 | 8/2010 | Hieb et al. |
| 2011/0009750 A1 | 1/2011 | Taylor et al. |
| 2011/0160681 A1 | 6/2011 | Dacey et al. |
| 2011/0196291 A1 | 8/2011 | Vischer et al. |
| 2011/0224649 A1 | 9/2011 | Duane et al. |
| 2011/0270091 A1 | 11/2011 | Hossack et al. |
| 2012/0181331 A1 | 7/2012 | Beden et al. |
| 2012/0253360 A1 | 10/2012 | White et al. |
| 2012/0302828 A1 | 11/2012 | Toledo-Crow et al. |
| 2013/0131579 A1 | 5/2013 | Mantell et al. |
| 2013/0253490 A1 | 9/2013 | Bitzer et al. |
| 2013/0338500 A1 | 12/2013 | Taylor et al. |
| 2014/0114298 A1 | 4/2014 | Taylor et al. |
| 2014/0275982 A1 | 9/2014 | Hendrick et al. |
| 2014/0276603 A1 | 9/2014 | Magee et al. |
| 2014/0276689 A1 | 9/2014 | Grace |
| 2014/0276690 A1 | 9/2014 | Grace |
| 2015/0011843 A1 | 1/2015 | Toth et al. |
| 2015/0141768 A1* | 5/2015 | Yu ........................ A61B 5/0084 600/301 |
| 2016/0184020 A1 | 6/2016 | Kowalewski et al. |
| 2016/0184021 A1 | 6/2016 | Kowalewski et al. |

FOREIGN PATENT DOCUMENTS

| | | |
|---|---|---|
| GB | 2208807 A | 4/1989 |
| WO | 1998019614 A1 | 5/1998 |
| WO | WO0057228 A2 | 9/2000 |
| WO | 2007115152 A2 | 10/2007 |
| WO | 2010042249 A4 | 8/2010 |

OTHER PUBLICATIONS

Wise et al. Evaluation of a Fiber Optic Glove for Semi-Automated Goniometric Measurements; Journal of Rehabilitation Research and Development vol. 27 No. 4, 1990, pp. 411-424.

Wollmann et al. Two Different Therapeutic Strategies in ICD Lead Defects: Additional Combined Lead Versus Replacement of the Lead; Journal of Cardiovascular Electrophysiology vol. 18, No. 11, Nov. 2007, pp. 1172-1177.

Yamamoto et al. Tissue Property Estimation and Graphical Display for Teleoperated Robot-Assisted Surgery; 2009 IEEE International Conference on Robotics and Automation, May 12, 17, 2009, 7 pages.

Yokoyama et al. Novel Contact Force Sensor Incorporated in Irrigated Radiofrequency Ablation Catheter Predicts Lesion Size and Incidence of Steam Pop and Thrombus Clinical Perspective; Circulation Arrhythmia and electrophysiology: Journal of the American Heart Association, Dec. 2008, pp. 353-362.

Yun et al. An Instrumented Glove for Grasp Specification in Virtual-Reality-Based Point and Direct Telerobotics; IEEE Transactions on Systems, Man, and Cybernetics—Bart B: Cybernetics, vol. 27, No. 5, Oct. 1997, pp. 835-846.

Zhan et al. Excess Length of Stay, Charges, and Mortality Attributable to Medical Injuries During Hospitalization; Journal of American Medical Association, vol. 290, No. 14, Oct. 8, 2003, pp. 1868-1874.

Griffin et al. Calibration and Mapping of a Human Hand for Dexterous Telemanipulation; ASME IMECE Conference, 2000, 8 pages.

Hager-Ross et al. Quantifying the Independence of Human Finger Movements: Comparisons of Digits, Hands, and Movement Frequencies; The Journal of Neurosciences, vol. 20 No. 22, Nov. 15, 2000, pp. 8542-8550.

Hajjarian et al. Intravascular Laser Speckle Imaging Catheter for the Mechanical Evaluation of the Arterial Wall; Journal of Biomedical Optics vol. 16(2) Feb. 2011, 7 pages.

Hanke et al. Morphological Changes and Smooth Muscle Cell Proliferation After Experimental Excimer Laser Treatment; Circulation vol. 83, 1991 pp. 1380-1389.

Hattori et al. Invivo Raman Study of the Living Rat Esophagus and Stomach Using a Micro-Raman Probe Under an Endoscope; Applied Spectroscopy vol. 61, No. 6, 2007, 8 pages.

Hauser Deaths and Cardiovascular Injuries Due to Device-Assisted Implantable Cardioverter-Defibrillator and Pacemaker Lead Extraction; Eurospace vol. 12, 2010, pp. 395-401.

Henning et al. An in Vivo Strain Gage Study of Elongation of the Anterior Cruciate Ligament; The American Journal of Sports Medicine, vol. 13, No. 1m 1985, pp. 22-26.

Inmann et al. An Instrument Object for Evaluation of Lateral Hand Grasp During Functional Tasks; Journal of Medical Engineering & Technology, vol. 25. No. 5, Sep./Oct. 2001, pp. 207-211.

Insull The Pathology of Atherosclerosis; Plaque Development and Plaque Responses to Medical Treatment; The American Journal of Medicine, vol. 122, No. 1A, Jan. 2009, 12 pages.

Jagsi et al. Original Investigation: Residents Report on Adverse Events and Their Causes; Arch Intern Med/ vol. 163 Dec. 12/26, 2005 7 pages.

Johns et al. Determination of Reduced Scattering Coefficient of Biological Tissue From a Needle-Like Probe; Optics Express vol. 13, No. 13. Jun. 27, 2005 pp. 4828-4842.

Kahol et al. "Effect of fatigue on psychomotor and cognitive skills." The American Journal of Surgery 195.2 (2008): 195-204.

Kane et al. A Traction Stress Sensor Array for Use in High-Resolution Robotic Tactile Imaging; Journal of Microelectromechanical Systems, vol. 9, No. 4, Dec. 2000, pp. 425-434.

Kang et al. A Carbon Nanotube Strain Sensor for Structural Health Monitoring; Smart Matter. Struct. vol. 15, 2006, pp. 737-748.

(56) References Cited

OTHER PUBLICATIONS

Karimov et al. A Carbon Nanotube-Based Pressure Sensor, Phys. Scr. 83, 2011, 5 pages.
Karsch et al. Percutaneous Coronary Excimer Laser Angioplasty Initial Clinical Results; The Lancet, Sep. 16, 1989 pp. 647-650.
Kennergren Excimer Laser Assisted Extraction of Permanent Pacemaker and ICD Leads: Present Experiences of a European Multi-Centre Study; European Journal of Cardio-Thoracic Surgery 15, 1990, pp. 856-860.
Khairy et al. Laser Lead Extraction in Adult Congenital Heart Disease; J. Cardiovasc Electrophysiol, vol. 18, 2006, pp. 507-511.
Khalil et al. Tissue Elasticity Estimation With Optical Coherence Elastography: Toward Mechanical Characterization of In Vivo Soft Tissue; Annals of Biomedical Engineering, vol. 33, No. 11, Nov. 2005, pp. 1631-1639.
Kochiadakis et al. The Role of Laser-Induced Fluorescence in Myocardial Tissue Characterization: An Experimental Invitro Study; Chest vol. 120, 2001, pp. 233-239.
Koulouris et al. Intravascular Lead Extractions: Tips and Tricks; Intech Open Science/Open Minds http//creativecommons.org/licenses/by/3.0, 2012 pp. 189-216.
Kremers et al. The National ICD Registry Report: Version 2.1 Including Leads and Pediatrics for Years 2010 and 2011; pp. 59-65.
Lathan et al. The Effects of Operator Spatial Perception and Sensory Feedback on Human-Robot Teleoperation Performance; Presence, vol. 11, No. 4, Aug. 2002, 368-377.
Levine et al. 2011 ACCF/AHA/SCAI Guideline for Percutaneous Coronary Intervention: Executive Summary; Journal of the American College of Cardiology vol. 58, No. 24, 2011, pp. 2250-2583.
Li et al. Strain and Pressure Sensing Using Single-Walled Carbon Nanotubes; Nanotechnology vol. 15, 2004, pp. 1493-1496.
Lieber et al. Sarcomere Length Determination Using Laser Diffraction: Effect of Beam and Fiber Diameter; Biophys J. vol. 45, May 1984, pp. 1007-1016.
Lipomi et al. Skin-Like Pressure and Strain Sensors Based on Transparent Elastic Films of Carbon Nanotubes; Nature Nanotechnology, vol. 6, Dec. 2011, pp. 788-792.
Maréchal, L. et al. "Measurement System for Gesture Characterization During Chest Physiotherapy Act on Newborn Babies Suffering from Bronchiolitis." Proceedings of the 29th Annual International Conference of the IEEE EMBS, Cité Internationale, Lyon, France. Aug. 23-26, 2007. pp. 5770-5773.
Maytin et al. Multicenter Experience With Extraction of the Sprint Fidelis Implantable Cardioverter-Defibrillator Lead; Journal of the American College of Cardiology vol. 56, No. 8, 2010, pp. 642-646.
Maytin et al. The Challenges of Transvenous Lead Extraction; Heart vol. 97, 2011, pp. 425-434.
Medtronic's Brochure; Implantable Pacemaker and Defibrillator Information; Apr. 2006, 2 pages.
Meier-Ewert et al. Endocardial Pacemaker or Defibrillator Leads With Infected Vegetations: A Single-Center Experience and Consequences of Transvenous Extraction; Am Heart Journal vol. 146, 2003, pp. 339-344.
Menciassi et al. Force Sensing Microinstrument for Measuring Tissue Properties and Pulse in Microsurgery, IEEE/ASME Transactions on Mechatronics, vol. 8, No. 1, Mar. 2003, pp. 10-17.
Mishra et al. Fiber Grating Sensors in Medicine: Current and Emerging Applications; Sensors and Actualtors A, 167, 2011, pp. 279-290.
Missinne Flexible Miniature Shear Sensors for Prosthetics; SPIE Newsroom SPIE, May 13, 2013, 4 pages.
Missinne, Jeroen et al. "Embedded Flexible Optical Shear Sensor." IEEE Sensors 2010 Conference. 2010. pp. 987-990.
Mond et al. The Electrode-Tissue Interface: The Revolutionary Role of Steroid Elution; Pace vol. 15, Jan. 1992, pp. 95-107.
Moscato et al. A Micromachined Intensity-Modulated Fiber Optic Sensor for Strain Measurements: Working Principle and Static Calibration; 34th Annual International Conference of the IEEE EMBS, 2012, pp. 5790-5793.
Mujat et al.; Automated Algorithm for Breast Tissue Differentiation in Optical Coherence Tomogrpahy; Journal of Biomedical Optics 14(3), 2009, 9 pages.
Neuzil et al. Pacemaker and ICD Lead Extraction With Electrosurgical Dissection Sheaths and Standard Transvenous Extraction Systems: Results of a Randomized Trial; Europace 9 , 2007, pp. 98-104.
Nikonovas et al. The Application of Force-Sensing Resistor Sensors for Measuring Forces Developed by the Human Hand; Proc. Instn Mech Engrs. vol. 218 Part H, 2004, 9 pages.
Nilsson et al Near Infrared Diffuse Reflection and Laser-Induced Fluorescence Spectroscopy for Myocardial Tissue Characterization; Spectrochimica ACTA Part A 53, 1997, pp. 1901-1912.
Noble et al. High Energy Excimer Laser to Treat Coronary In-Stent Restenosis in an Under Expanded Stent; Catheter and Cardiovascular Interventions vol. 71, 2008, pp. 803-807.
Noonan et al. A Dual-Function Wheeled Probe for Tissue Viscoelastic Property Identification During Minimally Invasive Surgery; IEEE International Conference on Robotics and Automation, Apr. 10-14, 2007, 6 pages.
Okumura et al. A Systematic Analysis of In Vivo Contact Forces on Virtual Catheter Tip/Tissue Surface Contact During Cardiac Mapping and Intervention; J. Cardiovasc Electrophysiol, vol. 19, Jun. 2008, pp. 632-640.
Orengo et al. Characterization of Piezoresistive Sensors for Goniometric Glove in Hand Prostheses; Wireless Vitae, 2009 pp. 684-687.
Park et al. Exoskeletal Force-Sensing End-Effectors With Embedded Optical Fiber-Bragg Grating Sensors; IEEE Transactions on Robotics, vol. 25, No. 6, Dec. 2009, pp. 1319-1331.
Park et al. Fingertip Force Control With Embedded Fiber Bragg Grating Sensors; IEEE conference on Robotics and Automation, May 19-23, 2008, pp. 3431-3436.
Park et al. Force Sensing Robot Fingers Using Embedded Fiber Bragg Grating Sensors and Shape Deposition Manufacturing; ; IEEE International Conference on Robotics and Automation, Apr. 10-14, 2007, . pp. 1510-1516.
Parker et al. Advanced Imaging Catheter Gives Surgeons the Inside Picture; Brochure Jun. 12, 2013: https//www.llnl.gov/str/DaSilva.html.
Patterson et al. Time Resolved Reflectance and Transmittance for the Non-Invasive Measurement of Tissue Optical Properties; Applied Optics vol. 28, No. 12, Jun. 15, 1989 pp. 2331-2336.
Peracchia Surgical Education in the Third Millennium; Annuals of Surgery, vol. 234, No. 6. 2001. pp. 709-712.
Pettit et al. Dynamic Optical Properties of Collagen-Based Tissue During ARF Excimer Laser Ablation; Applied Optics vol. 32, No. 4 Feb. 1, 1993, pp. 488-493.
Piers et al. A Micro Optical Force Sensor for Force Feedback During Minimally Invasive Robotic Surgery; Elsevier Sensors and Actuators A 115, 2004, pp. 447-455.
Polygerinos et al. MRI-Compatible Fiber-Optic Force Sensors for Catheterization Procedures; IEEE Sensors Journal vol. 10 No. 10, Oct. 2010, pp. 1598-1608.
Post et al.; Outcome After Complete Percutaneous Removal of Infected Pacemaker Systems and Implantable Cardiac Defibrillators; Internal Medicine Journal 36, 2006, pp. 790-792.
Prasad et al. A Modular 2-DOF Force-Sensing Instrument for Laparoscopic Surgery; MICCAI 2003, LNCS 2878 pp. 279-286.
Puangmali et al. State-Of-The Art in Force and Tactile Sensing for Minimally Invasive Surgery; IEEE Sensors Journal vol. 8, No. 4, Apr. 2008, pp. 371-381.
Rajan et al. Photonic Crystal Fiber Sensors for Minimally Invasive Surgical Devices; IEEE Transactions on Biomedical Engineering, vol. 59, No. 2, Feb. 2012, pp. 332-338.
Reiley et al. Review of Methods for Objective Surgical Skill Evaluation Surg Endosc, vol. 25, 2011 pp. 356-366.
Richards et al. Skills Evaluation in Minimally Invasive Surgery Using Force/Torque Signatures; Surg Endosc vol. 14, 2000, pp. 791-798.
Rinaldi et al. Determinants of Procedural Outcome of Chronically Implanted Pacemaker and Defibrillator Leads Using the Excimer Laser Sheath Heart.bmj.com, Dec. 5, 2012, 3 pages.
Rocha et al. Fluorescence and Reflectance Spectroscopy for Identification of Atherosclerosis in Human Carotid Arteries Using

(56) References Cited

OTHER PUBLICATIONS

Principal Components Analysis; Photomedicine and Laser Surgery vol. 26, No. 4, 2008, pp. 329-335.
Rosen et al. Markov Modeling of Minimally Invasive Surgery Based on Tool/tissue Interaction and Force/Torque Signatures for Evaluating Surgical Skills; IEEE Transactions on Biomedical Engineering, vol. 48, No. 5 May 2001, 13 pages.
Rovithakis Artificial Neural Networks for Discriminating Pathologic From Normal Peripheral Vascular Tissue; IEEE Transactions on Biomedical Engineering, vol. 48, No. 10, Oct. 2001 pp. 1088-1097.
Ruttmann et al. Transvenous Pacemaker Lead Removal is Safe and Effective Even in Large Vegetations: An Analysis of 53 Cases of Pacemaker Lead Endocarditis; PACE vol. 26, Mar. 2006 pp. 231-236.
Sangpradit et al. Tissue Identification Using Inverse Finite Element Analysis of Rolling Indentation; 2009 IEEE International Conference on Robotics and Automation; Kobe, Japan, May 12, 17, 2009, 6 pages.
Schroeder et al. Visualizing Surgical Training Databases: Exploratory Visualization, Data Modeling, and Formative Feedback for Improving Skill Acquisition: IEEE Computer Graphics and Applications, 2011, 11 pages; DOI 10.1109/MCG.2012.67.
Seibold et al. Prototype of Instrument for Minimally Invasive Surgery With 6-Axis Force Sensing Capability ; Proceedings of the 2005 IEEE International Conference on Robotics and Automation, Apr. 2005, 6 pages.
Sensor-Response-Compressive Force versus CNT sensor readout Chart, 2 pages.
Shah et al. Evaluation of a New Catheter Sensor for Real-Time Measurement of Tissue Contact; Heart Rhythm, vol. 3, No. 5, Supplement, May 2006 pp. S75-S76.
Simone et al. A Low Cost Instrumented Glove for Extended Monitoring and Functional Hand Assessment; Journal of Neuroscience Methods 160, 2007 pp. 335-348.
Smith et al. Extraction of Transvenous Pacing and ICD Leads; Pace vol. 31 Jun. 2008 pp. 736-752.
Sohail et al. Management and Outcome of Permanent Pacemaker and Implantable Cardioverter-Defibrillator Infections; Journal of the American College of Cardiology, vol. 49, No. 18, 2007 pp. 1851-1859.
Sokollik et al. New Model for Skills Assessment and Training Progress in Minimally Invasive Surgery; Surg Endosc vol. 18, 2004, pp. 495-500.
Sosa et al. The Importance of Surgeon Experience for Clinical and Economic Outcomes From Thyroidectomy; Annals of Surgery vol. 228, No. 3 pp. 320-330.
Spectranetics User Manual VisiSheath Dilator Sheath, 2011, 112 Pages.
Spectranetics Vascular Intervention ELCA: Coronary Laser Atherectomy Catheter Brochure (2012), 3 pages.
Spectranetics X80 User Manual ELCA Coronary Laser Atherectomy Catheter. Mar. 2012, 16 pages.
SPI2006 Shear Sensor Brochure—Real-Time Surface Shear Sensing Application: Human Interface; Tactilus Technology, 2006, 1 page.
Sturman et al. A Survey of Glove-Based Input; Clumsy Intermediary Devices Constrain Our Interaction With Computers and Their Applications. Glove-Based Input Devices Let Us Apply Our Manual Dexterity to the Task: IEEE Computer Graphics & Applications, Jan. 1994. pp. 30-39.
Sun et al. A Sub-Millemetric, 0.25 Mn Resolution Fully Integrated Fiber-Optic Force Sensing Tool for Retinal Microsurgery; Int J Comput Assist Radiol Surg. vol. 4(4): Jun. 2009, pp. 383-390.
Takano et al. Changes in Coronary Plaque Color and Morphology by Lipid-Lowering Therapy With Atorvastatin: Serial Evaluation by Coronary Angioscopy; The Journal of the American College of Cardiology, vol. 42, No. 4, 2003 pp. 680-686.
Taroni et al. In Vivo Absorption and Scattering Spectroscopy of Biological Tissues; Photochem. Photobiol. Sci. vol. 2, 2003. pp. 124-129.
Turchin et al. Novel Algorithm of Processing Optical Coherence Tomography Images for Differentiation of Biological Tissue Pathologies; Journal of Biomedical Optics 10(6), Nov./ Dec. 2005, 11 pages.
Turner et al. Development and Testing of a Telemanipulation System With Arm and Hand Motion; Accepted to 2000 ASME IMECE Symp. Haptic Interfaces, 2000, 7 pages.
Valdastri et al. Integration of a Miniaturized Triaxial Force Sensor in a Minimally Invasive Surgical Tool; IEEE Transactions on Biomedical Engineering, vol. 53, No. 11, Nov. 2006 pp. 2397-2400.
Van der Meer et al. Quantitative Optical Coherence Tomography of Arterial Wall Components; Lasers in Medical Science vol. 20, 2005, pp. 45-51.
Van der Meijden et al. The Valve of Haptic Feedback in Conventional and Robot-Assisted Minimal Invasive Surgery and Virtual Reality Training: A Current Review; Surg. Endosc vol. 23, 2009. pp. 1180-1190.
Van Leeuwen et al. Origin of Arterial Wall Dissections Induced by Pulsed Excimer and Mid-Infrared Laser Ablation in the Pigl; Jacc vol. 19, No. 7, Jun. 1992, pp. 1610-1618.
Van Lindert et al. The Influence of Surgical Experience on the Rate of Intraoperative Aneurysm Rupture and Its Impact on Aneurysm Treatment Outcome; Surg Neurol vol. 56, 2001, pp. 151-158.
Wagner et al. The Role of Force Feedback in Surgery: Analysis of Blunt Dissection; Presented at the Tenth Symposium on Haptic Interfaces for Virtual Environment and Teleoperator Systems, Mar. 24, 25, 2002, 7 pages.
Walker et al. Surgical Safety Checklists: Do They Improve Outcomes?; British Journal of Anaesthesia, 2012, pp. 1-8.
Wang et al. Characterization of a Silicon=Based Shear-Force Sensor on Human Subjects; IEEE Trans Biomed Eng., 2002 1 page.
Wang et al. Miniature All-Silica Optical Fiber Pressure Sensor With an Ultrathin Uniform Diaphragm; Optics Express vol. 18, No. 9, Apr. 26, 2010 pp. 9006-9014.
Wang et al. Review: The Physiological and Computational Approaches for Atherosclerosis Treatment; IJCA-15372, 2012, 13 pages.
Wang, Lin et al. "Characterization of a Silicon-Based Shear-Force Sensor on Human Subjects." IEEE Transactions on Biomedical Engineering, vol. 49, No. 11. Nov. 2002. pp. 1340-1347.
Wazni et al. Lead Extraction in the Contemporary Setting: The Lexicon Study; Journal of the American College of Cardiology vol. 55, No. 6, 2010, pp. 579-586.
Weiss et al. Muscular and Postural Synergies of the Human Hand; J. Neurophysiol 92, 2004 pp. 523-535.
Wilkoff et al. Transvenous Lead Extraction: Heart Rhythm Society Expert Consensus on Facilities, Training, Indications, and Patient Management; Heart Rhythm, vol. 6, No. 7, Jul. 2009, pp. 1086-1104.
Abeysinghe et. Al. A Novel MEMS Pressure Sensor Fabricated on an Optical Fiber; IEEE Photonics Technology Letters vol. 13. No. 9 Sep. 2001 pp. 993-995.
Agency for Healthcare Research and Quality Adjunctive Devices in PCI to Remove Thrombi or Protect Against Distal Embolization in Patients With ACS: A Clinician Research Summary; Effective Health Care Program; AHRQ Pub. No. 11 (12)-EHC089—May 3, 2012 4 pages.
Arifler et. Al. Light Scattering From Collagen Fiber Networks: Micro-Optical Properties of Normal and Neoplastic Stroma; Biophysical Journal vol. 92 May 2007, pp. 3260-3274.
Ashok et al. Raman Spectroscopy Sensor for Surgical Robotics—Instrumentation and Tissue Differentiation Algorithm Biomedical Optics and 3D Imaging OSA 2012 4 pages.
Bach et al., Design and Fabrication of 60-Gb/s InP-Based Monolithic Photoreceiver OEICs and Modules, IEEE Journal of Selected Topics in Quantum Electronics, vol. 8, No. 6, Nov. 1, 2002, 6 pgs.
Baddour et al. Update on Cardiovascular Implantation Electronic Device Infections and Their Management: A Scientific Statement From the American Heart Association Circulation 121: Jan. 2010, pp. 458-477.
Badr et al. The State of the Excimer Laser for Coronary Intervention in the Drug-Eluting Stent Era Cardiovascular Revascularization Medicine 14, 2013, pp. 93-98.

(56) References Cited

OTHER PUBLICATIONS

Bann et al. Attitudes Towards Skills Examinations for Basic Surgical Trainees J. Clin Pract Jan. 2005, 59, 1. pp. 107-113.
Baztarrica et al. Transvenous Extraction of Pacemaker Leads in Infective Endocarditis With Vegetations ≥ 20MM: Our Experience; Clinl. Cardiol 35, 4, 2012 pp. 244-249.
Beauvoit et al. Contribution of the Mitochondrial Compartment to the Optical Properties of the Rat Liver: A Theoretical and Practical Approach Biophysical Journal vol. 67 Dec. 1994 pp. 2501-2510.
Beccai et al. Design and Fabrication of a Hybrid Silicon Three-Axial Force Sensor for Biomechanical Applications; Sensors and Actuators A 120, 2005, pp. 370-382.
Berkelman et al. A Miniature Microsurgical Instrument Tip Force Sensor for Enhanced Force Feedback During Robot-Assisted Manipulation; IEEE Transactions on Robotics and Automaton, vol. 19, No. 5, Oct. 2003, pp. 917-922.
Bilodeau et al. Novel Use of a High-Energy Excimer Laser Catheter for Calcified and Complex Coronary Artery Lesions Catheterization and Cardiovascular Interventions 62: 2004 pp. 155-161.
Bindig et al. Fiber-Optical and Microscopic Detection of Malignant Tissue by Use of Infrared Spectrometry Journal of Biomedical Optics vol. 7 No. 1 Jan. 2002 pp. 100-108.
Bishop et al. Paid Malpractice Claims for Adverse Events in Inpatient and Outpatient Settings; JAMA vol. 205 No. 23 Jun. 15, 2011, pp. 2427-2431.
Bittl et al. Meta-Analysis of Randomized Trials of Percutaneous Transluminal Coronary Angioplasty Versus Atherectomy, Cutting Balloon Atherotomy, or Laser Angioplasty Journal of the American College of Cardiology vol. 43 No. 6 2004 pp. 936-942.
Bongiomi et al. Transvenous Removal of Pacing and Implantable Cardiac Defibrillating Leads Using Single Sheath Mechanical Dilatation and Multiple Venous Approaches; High Success Rate and Safety in More Than 200 Leads; European Heart Journal vol. 29, 2008, pp. 2886-2893.
Bracke et al. Pacemaker Lead Complications: When Is Extraction Appropriate and What Can We Learn From Published Data? Heart 2001 vol. 85 pp. 254-259.
Brennan et al. Analysis of Errors Reported by Surgeons at Three Teaching Hospitals, Surgery vol. 3, No. 6, 2003 pp. 614-621.
Britton Chance Optical Method; Annu Rev. Biophys. Chem vol. 20 1991 pp. 1-30.
Buch et al. Pacemaker and Defibrillator Lead Extraction; Circulation 2011:123 pp. 378-380.
Byrd et al. Clinical Study of the Laser Sheath for Lead Extraction: The Total Experience in The United States; Journal of Pacing and Clinical Electrophysiology, vol. 25 No. 5, May 2002 pp. 804-808.
Byrd et al. Intravascular Lead Extraction Using Locking Stylets and Sheaths; Pace vol. 13 Dec. 1990, pp. 1871-1875.
Candefjord et al. Combining Fibre Optic Raman Spectroscopy and Tactile Resonance Measurement for Tissue Characterization; Meas. Sci Technol. vol. 21, 2010 125801 8 pages.
Candinas et al. Postmortem Analysis of Encapsulation Around Long-Term Ventricular Endocardial Pacing Leads; Mayo Clin Proc. vol. 74, Feb. 1999, pp. 120-125.
Carlson et al. Motion Capture Measures Variability in Laryngoscopic Movement During Endotracheal Intubation: A Preliminary Report; 2012 Society for Simulation in Healthcare, vol. 7, No. 1, Aug. 2012 pp. 255-260.
Chan et al. Effects of Compression on Soft Tissue Optical Properties; IEEE Journal of Selected Topics in Quantum Electronics, vol. 2 No. 4, Dec. 1996 pp. 943-950.
Cheong et al. A Review of the Optical Properties of Biological Tissues; IEEE Journal of Quantum Electronics vol. 26, No. 12, Dec. 1990 pp. 2166-2185.
Chung, Kit Man. Advanced Fibre Bragg Grating and Microfibre Bragg Grating Fabrication Techniques; A Thesis Submitted in Partial Fulfillment of the Requirements for the Degree of Doctor of Philosophy, The Hong Kong Polytechnic University; Mar. 2012 (abstract of thesis/document attached; full printed version of thesis/document unavailable; entire online version of thesis/document available at http://repository.lib.polyu.edu.hk/jspui/handle/10397/5524).
Cruz et al. Internal Mammary Arterial Injury From Lead Extraction: A Clinically Subtle Yet Important Complication of Implantable Device Removal; Cardiology Research and Practice vol. 2011, Article ID 408640, (2011) 5 pages.
Da et al. Overview of the Vascular Interventional Robot; The International Journal of Medical Robotics and computer assisted surgery 2008;4: pp. 289-294.
Dallon et al. A Mathematical Model for Spatially Varying Extracellular Matrix Alignment; SIAM J. Appl. Math. vol. 61, No. 2, 2000, pp. 506-527.
Deharo et al. Pathways for Training and Accreditation for Transvenous Lead Extraction: A European Heart Rhythm Association Position Paper; Europace 14 (2012) pp. 124-134.
Dipietro et al. Evaluaton of an Instrumented Glove for Hand-Movement Acquisition; Journal of Rehabilitation Research and Development vol. 40, No. 2, Mar./Apr. 2003, pp. 179-190.
Eichhorn et al. Carbon Nanotube Filled Composite Material Analysis Utilizing Nano and Conventional Testing Techniques; NIP & Digital Fabrication Conference, 2010 International Conference on Digital Printing Technologies. 5 Pages.
Eichhorn et al. Flexible Carbon Nanotube Composite Sensors for Medical Device Application; J. Med. Devices 7(2), 020943 (Jun. 11, 2013) (2 pages)Paper No. MED-13/1050; doi: 10.1115/1.4024311.
ELCA Coronary Laser Atherectomy Catheter Brochure, Spectranetics, 2012.
El-Sawah et al. A Prototype for 3-D Hand Tracking and Posture Estimation; IEEE Transactions on Instrumentation and Measurement, vol. 57, No. 8, Aug. 2008, pp. 1627-1636.
Endo et al. Clinical Utility of Intraprocedural Transesophagael Echocardiography During Transvenous Lead Extraction; Journal of the American Society of Echocardiography vol. 21 No. 7, Jul. 2008 pp. 862-867.
Epstein et al. Gross and Microscopic Pathological Changes Associated With Nonthoracotomy Implantable Defibrillator Lead; Circulation 1998:98: 1517-1524.
Erturk et al. Outcome of Surgery for Acromegaly Performed by Different Surgeons: Importance of Surgical Experience; Pituitary 8: 2005, pp. 93-97.
Esenaliev et al. Laser Ablation of Atherosclerotic Blood Vessel Tissue Under Various Irradiation Conditions; IEEE Transactions on Biomedical.
Esposito et al. Morphologic and Immunohistochemical Observations of Tissues Surrounding Retrieved Transvenous Pacemaker Leads; Wiley Periodicals, Inc. 2002, pp. 548-558.
Faber et al. Light Absorption of (OXY—) Hemoglobin Assessed by Spectroscopic Optical Coherence Tomography; Optics Letters vol. 28, No. 16, Aug. 15, 2003 pp. 1436-1438.
Fanson et al. A System for Laparoscopic Surgery Ergonomics and Skills Evaluation; Journal of Endourology vol. 25, No. 7, Jul. 2011 pp. 1111-1114.
U.S. Appl. No. 09/947,171, filed Sep. 4, 2001, 71 pages.
FSR: Force Sensing Resistor Integration Guide and Evaluation Parts Catalog: 400 Series Evaluation Parts With Suggested Electrical Interfaces; Interface Electronics; Version 1.0 (90-45632 Rev. D), 26 pages.
Fung et al. A PMMA-Based Micro Pressure Sensor Chip Using Carbon Nanotubes as Sensing Elements; IEEE International Conference on Micro Electro Mechanical Systems, vol. 18, 2005 pp. 251-254.
Ghosh et al. Laser Lead Extraction: Is There a Learning Curve?; Pace, vol. 28; Mar. 2005 pp. 180-184.
Golzio et al. Prevention and Treatment of Lead Extraction Complications; Transvenous Lead Extraction; Springer-Verlag Italia 2011 pp. 129-136.
Advisory Action issued in U.S. Appl. No. 12/337,232, dated Aug. 8, 2013, 3 pages.
European Search Report issued in EP Application No. 05796879.4 dated Mar. 6, 2008, 7 pages.
European Search Report issued in EP Application No. 08010688.3. dated Feb. 17, 2009, 6 pages.

(56) References Cited

OTHER PUBLICATIONS

Final Official Action for U.S. Appl. No. 12/337,232 dated Apr. 23, 2013, 11 pages.
Grundfest, Warren S., MD, et al., "Laser Ablation of Human Atherosclerotic Plaque Without Adjacent Tissue Injury," JACC vol. 5, No. 4, (Apr. 1985), pp. 929-933.
International Preliminary Report on Patentability issued in PCT/US2009/066133, dated Jun. 21, 2011, 8 pages.
International Search Report and Written Opinion issued in PCT/2014/019258, dated Aug. 8, 2014, 21 pages.
International Search Report and Written Opinion issued in PCT/2014/019283, dated Jun. 20, 2014, 15 pages.
International Search Report and Written Opinion issued in PCT/2014019278, dated May 7, 2014, 14 pages.
International Search Report and Written Opinion issued in PCT/US2005/033029, dated Oct. 3, 2006, 1 page.
International Search Report and Written Opinion issued in PCT/US2009/066133, dated Jan. 26, 2010, 8 pages.
Notice of Allowance for U.S. Appl. No. 12/649,759 dated May 16, 2013, 12 pages.
Notice of Allowance for U.S. Appl. No. 11/228,845 dated Jun. 5, 2009, 8 pages.
Notice of Allowance for U.S. Appl. No. 12/406,807 dated Aug. 2, 2010, 7 pages.
Notice of Alowance for U.S. Appl. No. 12/337,232 dated Sep. 6, 2013, 11 pages.
Official Action for U.S. Appl. No. 11/228,845 dated Jan. 12, 2009, 13 pages.
Official Action for U.S. Appl. No. 11/228,845 dated Sep. 3, 2008, 10 pages.
Official Action for U.S. Appl. No. 12/337,232 dated Mar. 23, 2012, 9 pages.
Official Action for U.S. Appl. No. 12/337,232 dated Sep. 13, 2012, 10 pages.
Official Action for U.S. Appl. No. 12/649,759 dated Aug. 30, 2012, 11 pages.
Official Action for U.S. Appl. No. 12/649,759 dated Jul. 16, 2012, 9 pages. (Restriction Requirement).
U.S. Appl. No. 14/586,529, filed Dec. 30, 2014.
U.S. Appl. No. 14/586,543, filed Dec. 30, 2014.
Wikipedia, Linear discriminant analysis, Dec. 21,2013, http://en.wikipedia.org/wiki/Linear_discriminant_analysis.
Extended European Search Report issued in European Patent Application 14773432.1, dated Oct. 4, 2016.

\* cited by examiner

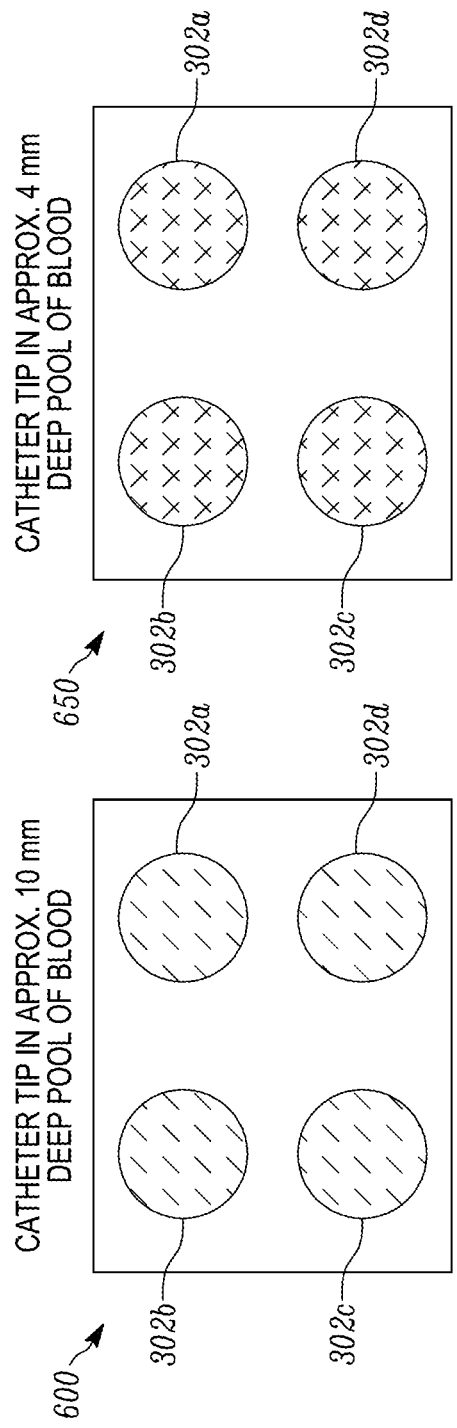
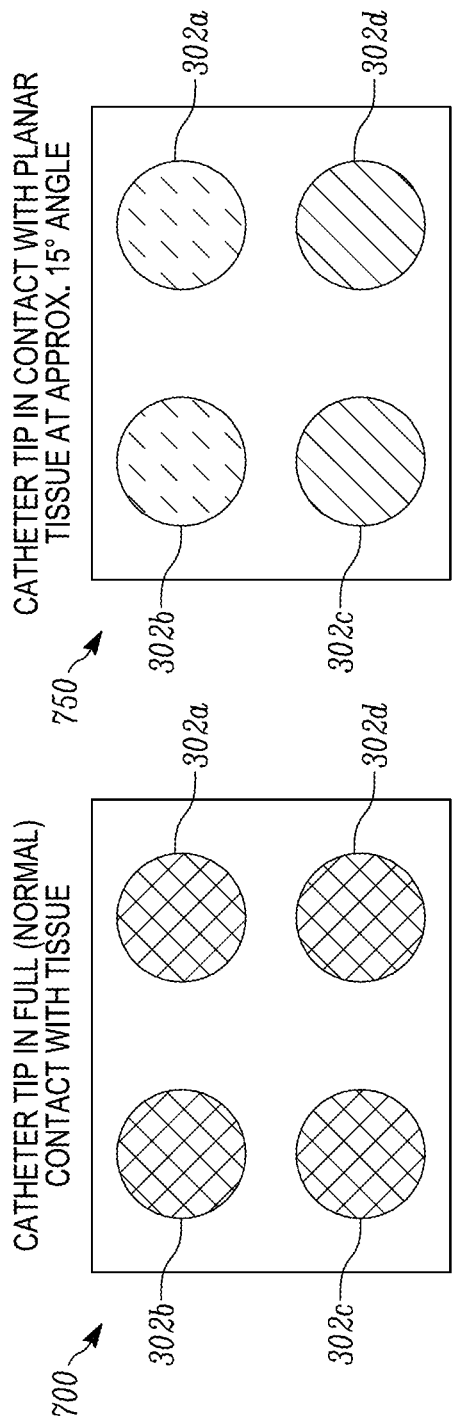

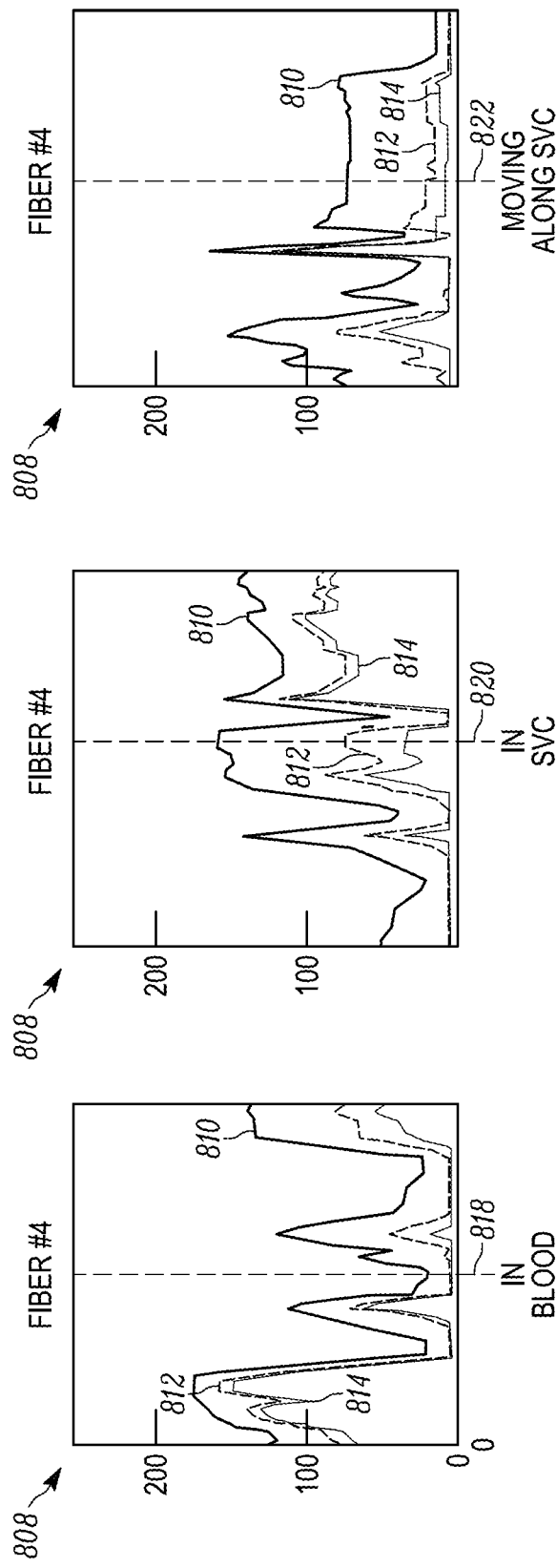

LASER CATHETER WITH USE OF REFLECTED LIGHT TO DETERMINE MATERIAL TYPE IN VASCULAR SYSTEM

CROSS-REFERENCES TO RELATED APPLICATIONS

The present application is related to U.S. patent application Ser. No. 14/586,529, entitled "LASER CATHETER WITH USE OF DETERMINED MATERIAL TYPE IN VASCULAR SYSTEM IN ABLATION OF MATERIAL," which is filed on the same day as the present application and the contents of which are incorporated by reference herein for all that it discloses. The present application is also related to U.S. patent application Ser. No. 14/586,543, entitled "LASER CATHETER WITH USE OF REFLECTED LIGHT AND FORCE INDICATION TO DETERMINE MATERIAL TYPE IN VASCULAR SYSTEM," which is filed on the same day as the present application and the contents of which are incorporated by reference herein for all that it discloses.

FIELD

The present disclosure relates generally to medical devices, and, more particularly, to laser catheters used in treatment within a vascular system and the use of reflected light associated with a laser catheter to determine a type of a material within a vascular system.

BACKGROUND

Electrical leads, such as those used with pacemakers, defibrillators, etc., are implanted in the human vascular system and often experience a buildup of unwanted deposits thereon, such as plaque, calcified tissue, and the like. Additionally, human blood vessels often become occluded or blocked by plaque, thrombi, other deposits, emboli, etc., which reduce the blood carrying capacity of such vessels. Should a blockage occur at a critical place in the vascular system of a patient, serious and permanent injury, and even death, can occur. To prevent damage to electrical leads, and to prevent damage elsewhere in the vascular system, some form of medical intervention is usually performed when a buildup or significant occlusion is detected.

Laser-based catheter devices are often used to ablate such buildups or occlusions. Laser light is sent down optical fibers of a laser catheter to perform laser ablation and, in some cases, visualization of vascular structure. Additionally, fluoroscopy presents a two-dimensional view and, in cases where contrast agents are injected, provides indirect visualization of vascular structure. Fluoroscopy is a procedure that may introduce undesirable radiation exposure and risks associated with the use of contrast agents, and may also provide insufficient imaging or feedback for clinicians to clearly understand the interface between the catheter device and the vascular system. As a result, with a fluoroscopy procedure, there is a risk of errors in determining whether or not contacted tissue should be ablated, errors in determining how much undesired tissue remains during or after ablation, and potential overtreatment including tearing of tissue.

SUMMARY

These and other needs are addressed by the various aspects, embodiments, and configurations of the present disclosure.

According to one embodiment of the present disclosure, an apparatus for determining a type of a material in a region within a vascular system of a patient may include a laser catheter and at least one controller. The laser catheter may be coupled to a light source and may include at least one source fiber configured to supply light from the light source to a region within a vascular system of a patient so as to illuminate the region within the vascular system of the patient. The laser catheter may also include at least one return fiber configured to receive light reflected from the region within the vascular system of the patient, where the reflected light may be indicative of at least one of a transmittance, a reflectance, an absorbance, and a scattering coefficient of the region within the vascular system of the patient. The at least one controller may be configured to determine the at least one of the transmittance, the reflectance, the absorbance, and the scattering coefficient of the region within the vascular system of the patient. The at least one controller may be further configured to determine a type of a material in the region within the vascular system based on determining the at least one of the transmittance, the reflectance, the absorbance, and the scattering coefficient of the region within the vascular system.

According to another embodiment of the present disclosure, an apparatus for determining a type of a material in a region within a vascular system of a patient and a distance to the material may include a laser catheter and at least one controller. The laser catheter may be coupled to a light source and may include at least one source fiber configured to supply light from the light source to a region within a vascular system of a patient so as to illuminate the region within the vascular system of the patient. The laser catheter may also include at least one return fiber configured to receive light reflected from the region within the vascular system of the patient. The at least one controller may be configured to determine at least one property of the region within the vascular system from the reflected light from the region within the vascular system. The at least one controller may also be configured to determine a type of a material in the region within the vascular system based on determining the at least one property from the reflected light. The at least one controller may be further configured to determine an indication of a distance to the material in the region within the vascular system based on determining the at least one property from the reflected light.

According to yet another embodiment of the present disclosure, a method for determining a type of a material in a region within a vascular system of a patient may include receiving an output from at least one return fiber of a laser catheter, where the at least one return fiber receives light reflected from a region within a vascular system of a patient after at least one source fiber has supplied light to the region. The reflected light may be indicative of at least one of a transmittance, a reflectance, an absorbance, and a scattering coefficient of the region within the vascular system of the patient. The method may also include determining the at least one of the transmittance, the reflectance, the absorbance, and the scattering coefficient of the region within the vascular system of the patient. The method may further include determining a type of a material in the region within the vascular system of the patient based on determining the at least one of the transmittance, the reflectance, the absorbance, and the scattering coefficient of the region within the vascular system.

According to another embodiment of the present disclosure, a method for determining a type of a material in a region within a vascular system of a patient and a distance to the material may include receiving an output from at least one return fiber of a laser catheter, where the at least one return fiber receives light reflected from a region within a vascular system of a patient after at least one source fiber has supplied light to the region. The method may also include determining at least one property of the region within the vascular system from the reflected light from the region within the vascular system. The method may further include determining a type of a material in the region within the vascular system based on determining the at least one property from the reflected light. The method may also include determining an indication of a distance to the material in the region within the vascular system based on determining the at least one property from the reflected light.

According to yet another embodiment of the present disclosure, a non-transitory computer-readable medium may include executable instructions that when executed by one or more processors cause the one or more processors to generate, based on light reflected from a region within a vascular system of a patient after illumination of the region with light from a light source, at least one signal indicative of at least one property of the region within the vascular system. The executable instructions, when executed by the one or more processors, may also cause the one or more processors to determine, based on the generated at least one signal, the at least one property of the region within the vascular system. The executable instructions, when executed by the one or more processors, may further cause the one or more processors to determine a type of a material in the region within the vascular system based on determining the at least one property of the region.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

The terms "analyze", "determine", "calculate" and "compute", and variations thereof, as used herein, are used interchangeably and include any type of methodology, process, mathematical operation or technique.

A "laser emitter" refers to an end portion of a fiber or an optical component that emits laser light from a distal end of the catheter towards a desired target or region, which typically comprises tissue.

An optical fiber (or laser active fiber) is a flexible, transparent fiber made of an optically transmissive material, such as glass (silica) or plastic, which functions as a waveguide, or "light pipe", to transmit light between the two ends of the fiber.

The term "biological material" includes any living cell or cells, and any biomolecule associated with a living cell or cells (i.e., cell-based). Biological material includes both intracellular biomolecules and extracellular biomolecules. Biological material may include, for example, nucleic acids (i.e., RNA and DNA), amino acids (proteins and polypeptides), carbohydrates (e.g., sugars used for glycosylation), polysaccharides, lipids, and combinations thereof. In the context of the cardiovascular system, biological material includes biomolecules associated with the various cell types that make up the vasculature (e.g., endothelial cells and smooth muscle cells), such as cell surface receptors.

The term "non-biological material" includes any material that is not associated with a living cell or cells (i.e., non-cell-based). Non-biological material includes molecules typically found within an atherosclerotic occlusion and not the surrounding cells of the vasculature. Non-biological material found in atherosclerotic occlusions include, for example, fat deposits (e.g., cholesterol monohydrate, cholesterol esters, and phospholipids), fibrous tissue (e.g., fibrin, proteoglycans, collagen), calcium deposits (e.g., calcium oxide, calcium carbonate, calcium phosphates), and remnants of dead cells and cellular debris.

The term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIGS. 6A, 6B, 7A, and 7B are simplified views of reflected diffuse absorbance and transmittance (DAAT) characteristics from the perspective of outputs of return fibers;

FIGS. 8A-8C illustrate several magnified views of different portions of the video frame for one of the four return fibers of FIG. 8, including several magnified views of the example intensities shown in FIG. 8 of the red, green, and blue channels for the fiber and several of the example corresponding indications shown in FIG. 8 of type of a material and/or distance to a material;

DETAILED DESCRIPTION

Laser catheters typically transmit laser energy through optical fibers housed in a relatively flexible tubular catheter inserted into a body lumen, such as a part of the vasculature, ureter, fallopian tube, and the like to remove obstructions in the lumen. Catheters used for laser angioplasty and other procedures may have a central passageway or tube which receives a guide wire inserted into the body lumen (e.g., vasculature) prior to catheter introduction. The guide wire facilitates the advancement and placement of the catheter to the selected portion(s) of the body lumen for laser ablation of tissue.

Examples of laser catheters or laser sheath are sold by the Spectranetics Corporation under the trade names ELCA™ and Turbo Elite™ (each of which is used for coronary intervention or catheterization such as recanalizing occluded arteries, changing lesion morphology, and facilitating stent placement) and SLSII™ and GlideLight™ (which is used for surgically implanted lead removal). The working (distal) end of a laser catheter typically has a plurality of laser emitters, such as ends of source fibers, which emit energy and ablate the targeted tissue. The opposite (proximal) end of a laser catheter typically has a fiber optic coupler, which connects to a laser system or device or generator including a light source. One such example of a laser system is the CVX-300 Excimer Laser System, which is also sold by the Spectranetics Corporation.

Figure 1:
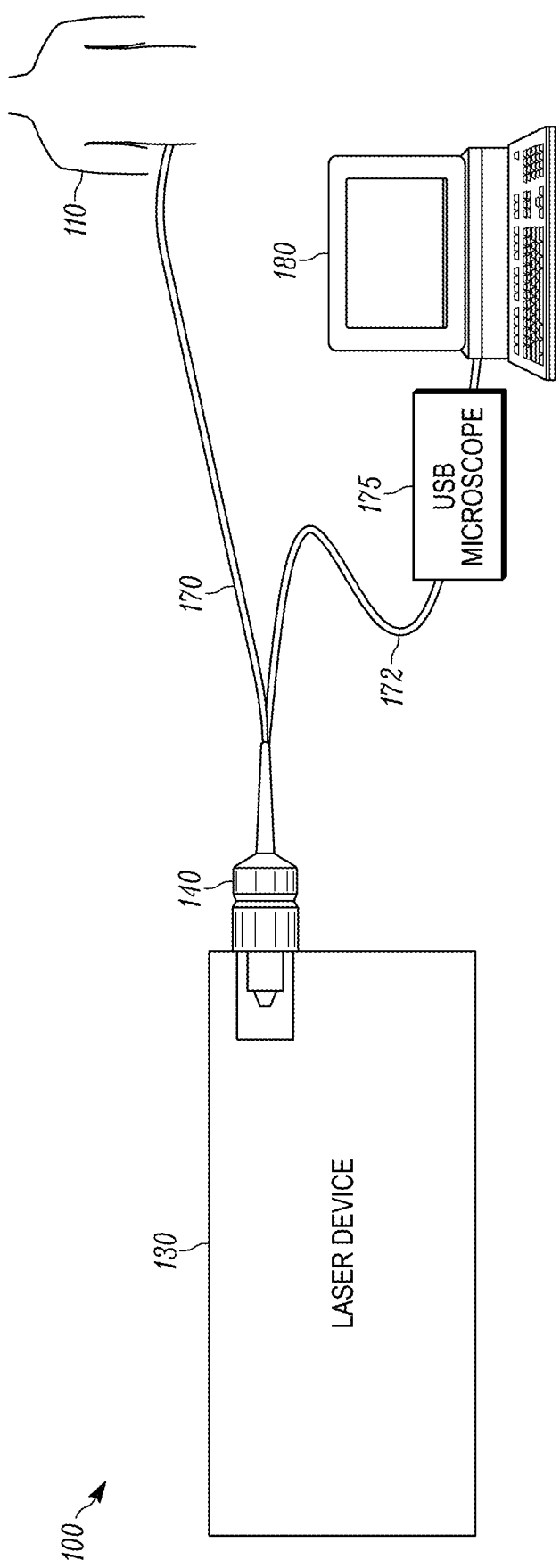
FIG. 1 shows an example apparatus for determining a type of a material in a region within a vascular system of a patient and a distance to the material.

Referring now to FIG. 1, an example apparatus 100 for determining a type of a material in a region within a vascular system of a patient and a distance to the material (e.g., to a boundary of the material, as further discussed below) is shown in accordance with one embodiment of the present disclosure. The example apparatus 100 is illustrated as generally including a laser device 130, which may include a light source such as a laser (e.g., an excimer laser or any suitable laser), coupled to a proximal end of a laser catheter 170 by way of a coupler 140.

In another embodiment, a separate light source for purposes of determining the type of the material and the distance to the material in the region within the vascular system of the patient, which may at times be referred to as a diagnostic light source, may be included in the laser device 130 and also coupled to the proximal end of the laser catheter 170 by way of, for example, the coupler 140. The diagnostic light source may be any suitable light source and need not be a laser. For example, the diagnostic light source may be or may include one or more light-emitting diodes (LEDs), broadband light source(s) (e.g., halogen light source(s)), xenon flash light source(s), etc. In such an implementation, the laser device 130 may still include at least one treatment light source, which may also be referred to as a therapeutic light source, such as a laser for ablating bodily material such as buildup of plaque, calcium deposits, scar tissue, or the like. The therapeutic/treatment light source may be adjusted (e.g., in intensity, in distance from tissue, etc., as further described below) based on the determined type of the material in the region and/or the distance to the material in the region. It will be understood in light of the following disclosure that references herein to "light source" may include either or both of (e.g., collectively) the therapeutic/treatment light source and a diagnostic light source.

The laser catheter 170 is also connected to at least one controller 180 by any suitable connection, such as, for example, by way of a wired connection via the coupler 140, a return connection portion 172, and if desired a device such as a USB microscope 175 to aid in producing images of the material in the region of the vascular system of the patient and/or other suitable data as discussed below. The laser catheter 170 may also be connected to the at least one controller 180 by any other suitable wired or wireless connection. While illustrated as a computing device, the at least one controller 180 may be implemented, for example, by executing suitable instructions on any suitable processor(s), by at least one digital signal processor, by one or more application-specific integrated circuits (ASICs), or by any other suitable hardware, firmware, or software implementation or any suitable combination of the example implementations described above. In another embodiment, the at least one controller 180 is connected to the laser device 130 and receives and/or analyzes reflected light from a region within the vascular system of the patient, as further described below, after such reflected light is received by the laser device 130. In yet another embodiment, the at least one controller 180 may be internal to the laser device 130.

As also illustrated in FIG. 1, a distal end of the laser catheter 170 may be inserted into a patient 110, such as into the vasculature of the patient 110. In some embodiments, the example apparatus 100 employs a plurality of fibers, such as optical fibers, as light guides that guide laser light from the laser device 130 through the laser catheter 170 and toward a target area or region within the vascular system of the patient 110.

Figures 2, 3:
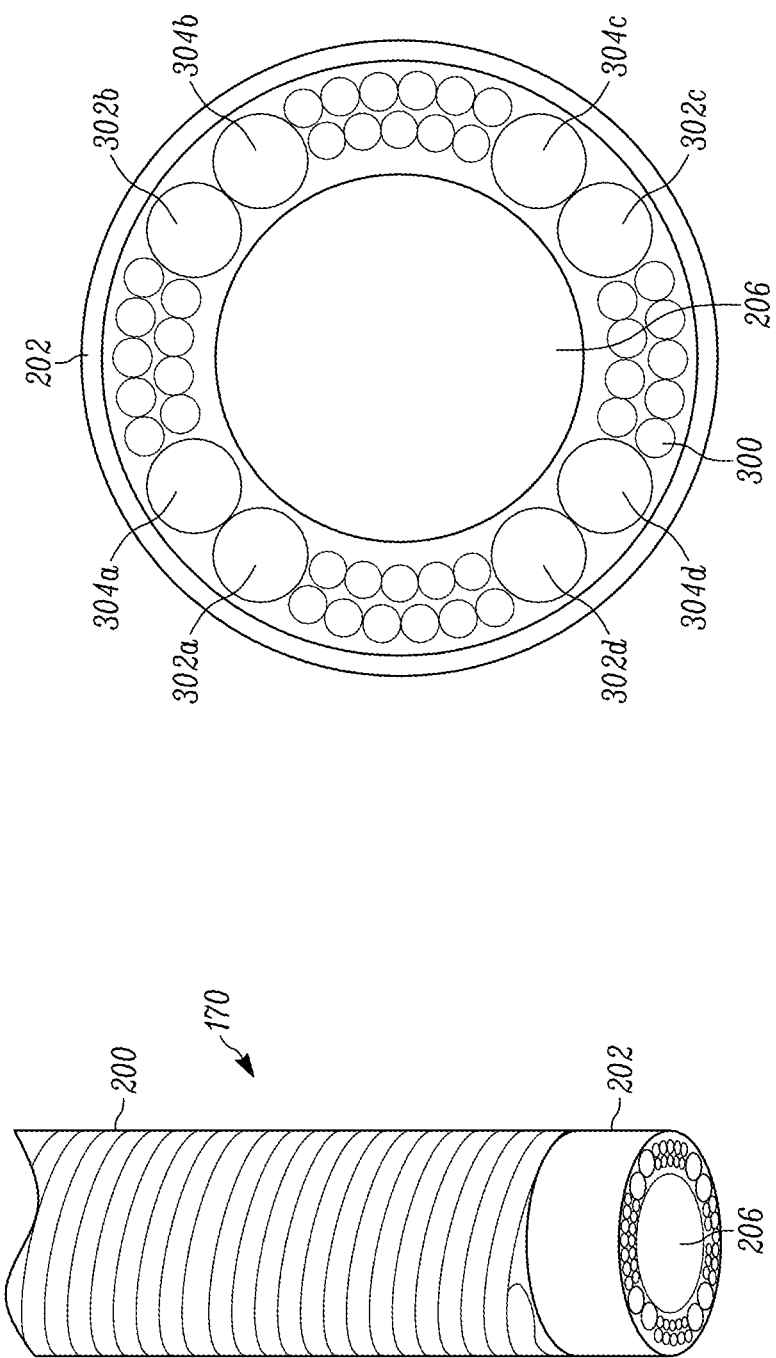
FIG. 2 is a top perspective view of a distal portion of a catheter, such as a laser catheter.
FIG. 3 is an elevation view of a distal portion of a catheter, such as a laser catheter.

FIGS. 2 and 3 are a top perspective view and an elevation view, respectively, of a distal portion of a catheter, such as the example laser catheter 170, according to an embodiment of the present disclosure. As shown in the example of FIGS. 2 and 3, the distal portion of the laser catheter 170 may include an outer jacket 200 or sleeve, and may include a distal end 202. The outer jacket 200 of the example of FIGS. 2 and 3 comprises a flexible assembly with the ability to resist user-applied forces such as torque, tension, and compression. The proximal end (not shown) of the laser catheter 170 is attached to a fiber optic coupler, such as the coupler 140 as shown in FIG. 1. The laser catheter 170 includes an outer jacket, inner band, and at least one optical fiber similar to the configuration and orientation of such components as shown in FIGS. 2 and 3 and further described herein. The distal end 202 of the laser catheter 170 comprises a plurality of optical fibers, including at least one source fiber acting as a laser emitter or emitters, and at least one return fiber as further described below. The energy emitted by the laser emitter(s) cuts, separates, and/or ablates the scar tissue, plaque build-up, calcium deposits, and other types of undesirable lesion or bodily material within the vascular system of the patient 110.

The distal end 202 of the laser catheter 170 may, in some embodiments, include a lumen 206. If the lumen 206 is included in the laser catheter 170, a clinician may insert the laser catheter 170 into the vasculature over a guidewire (not shown) through the lumen 206. It may, however, be preferable for the laser catheter 170 to have a separate guidewire lumen. Incorporation of such a guidewire lumen is generally known to one of ordinary skill in the art, and all such guidewire lumens within the knowledge of one skilled in the art are considered within the scope of the present disclosure. The lumen 206 may also be used to slide the laser catheter 170 over an electrical lead in a lead removal procedure. The lumen may also include one or more fixed and/or removable conduit(s) for additional tools to assist in tissue removal or navigation, such as but not limited to optical coherence tomography (OCT) catheters or intravascular ultrasound (IVUS) catheters. The additional tools may assist in procedures associated with tissue removal or navigation such as saline injection, suction, balloon deployment, and/or use of injectable contrast agents that can amplify the sensed optical contrast of targeted tissue(s) so as to improve the ability to correctly discriminate such tissue(s).

The aforementioned laser emitter(s), as further described below, may be provided in a generally concentric configuration or in any other suitable configuration such as an eccentric configuration. For example, the lumen 206, in embodiments where the laser catheter includes the lumen 206, may be provided substantially concentric with and interior to the laser emitter(s) (and optical fiber(s)), or eccentric with respect to the laser emitter(s), thereby providing a potential conduit or passageway for translocation of materials cut or ablated by the laser emitter(s).

Although FIGS. 2 and 3 illustrate the laser emitter(s) in a generally concentric configuration, those skilled in the art will appreciate that there are numerous other ways and configurations (e.g., eccentric configurations, as discussed above) in which to arrange at least one laser emitter. Additionally, although these two figures illustrate an outer jacket 200 and a distal end 202, those of skill in the art will appreciate that distinct components need not be used, and the optical fibers may be encapsulated within a single sleeve. Accordingly, FIGS. 2 and 3, as well as FIG. 4 discussed below, are not intended to represent the only way that a laser catheter such as the laser catheter 170 may be configured and constructed, and all such configurations and constructions within the knowledge of one skilled in the art are considered within the scope of this disclosure.

With continued reference to FIG. 3, a more particular example implementation of the plurality of optical fibers is shown, according to an embodiment of the present disclosure. As shown in FIG. 3, the plurality of optical fibers may include at least one source fiber 300 configured to supply light from a light source to a region within the vascular system of a patient so as to illuminate the region, and at least one return fiber 302 configured to receive light reflected from the region, as further described below. In particular, the at least one source fiber may include one or, as shown, a plurality of source fibers 300. The at least one return fiber 302 may include one or, as shown, a plurality of return fibers 302a, 302b, 302c, and 302d. The plurality of optical fibers may, if desired, be implemented such that fewer return fibers than source fibers are used, and where the return fibers may have larger cross-sectional area. The return fiber(s) 302 may be evenly or unevenly spaced around, for example, a lumen 206 within the laser catheter 170. For example, if two return fibers 302 are used, the return fibers 302 may be spaced 180 degrees apart from one another; if three return fibers 302 are used, the return fibers 302 may be spaced 120 degrees apart from one another; and if four return fibers 302 are used as shown in FIG. 3, the return fibers 302 may be spaced 90 degrees apart from one another. In other embodiments, the return fibers 302 may not be evenly spaced with respect to one another in manners such as the example manners provided above. The plurality of optical fibers may also include at least one additional fiber 304 coupled to the light source (the light source being discussed above with respect to FIG. 1 and further below with respect to FIG. 5). The at least one additional fiber 304 may also be coupled, along with the source fiber(s) 300 and return fiber(s) 302, to the at least one controller 180 to enable the at least one controller 180 to use information from the additional fiber(s) 304 regarding light from the light source to determine an intensity of the light supplied by the source fiber(s) 300.

Figure 4:
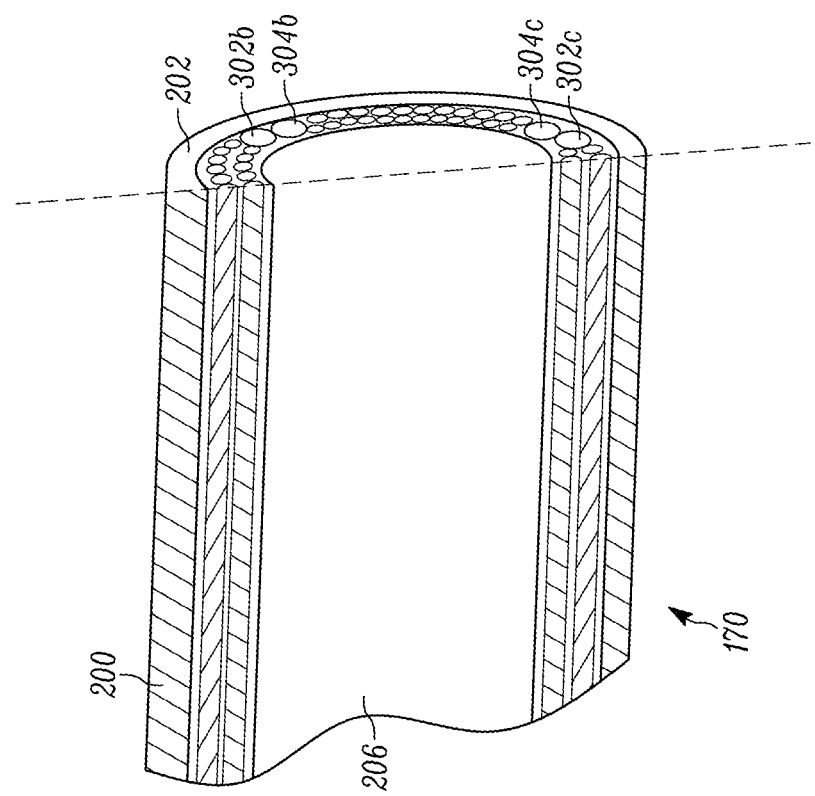
FIG. 4 is a cross-sectional perspective view of a distal portion of a catheter, such as a laser catheter.

FIG. 4 is a cross-sectional perspective view of a distal portion of a laser catheter, which may be used to implement the laser catheter 170, according to one embodiment of the present disclosure. As discussed above, the laser catheter 170 may include a distal end 202 that may, in some embodiments, include the lumen 206. The distal end 202 may be operable by a user, and the position of the distal end 202 is controlled by, for example, deflection means such as pullwires, shaping wires, and similar force-transmitting features controlled by the user at a user-proximal location of the laser catheter 170.

Figure 5:
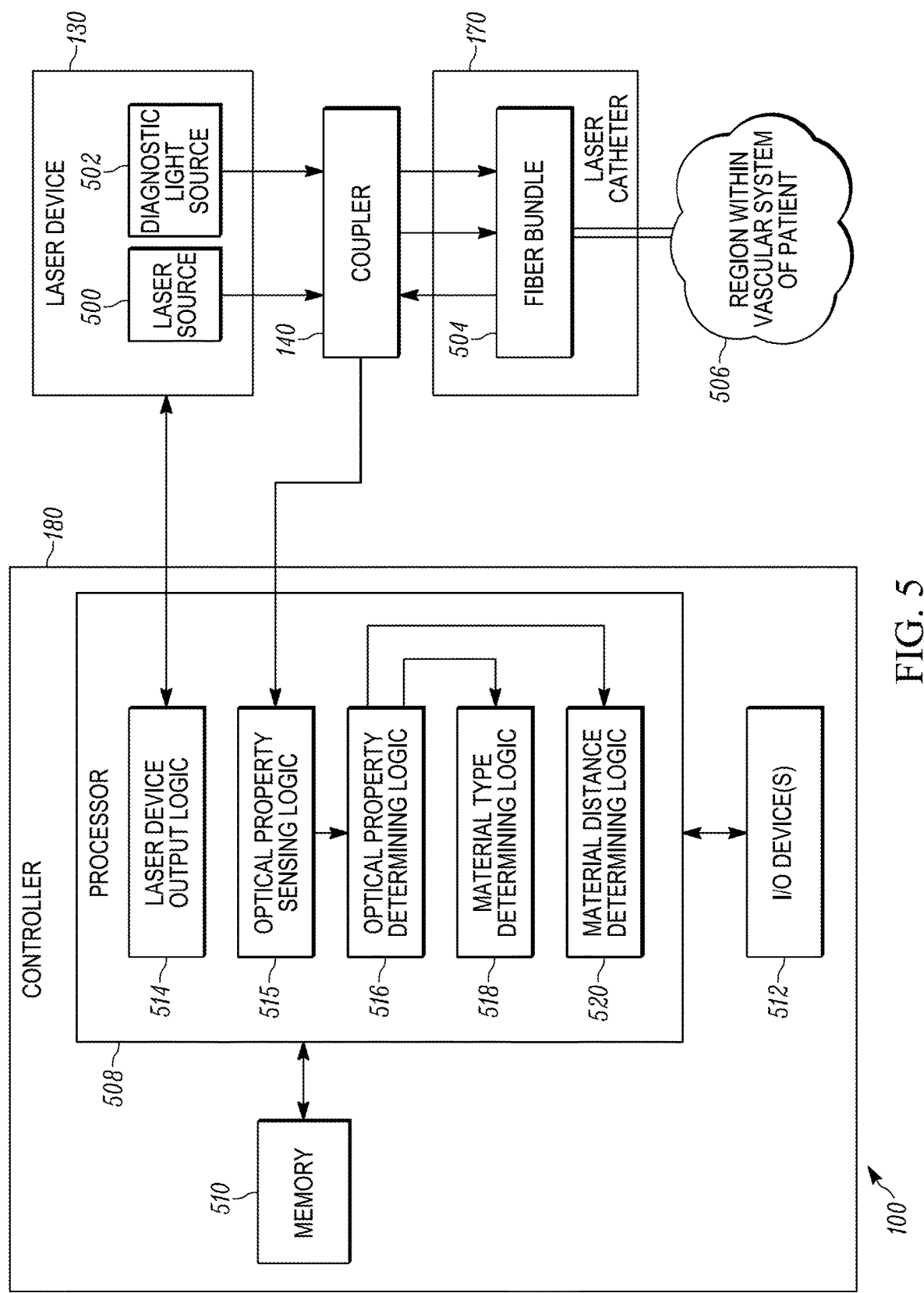
FIG. 5 is a functional block diagram of the example apparatus of FIG. 1.

FIG. 5 is a functional block diagram of the example apparatus 100 for determining a type of a material in a region within a vascular system of a patient and a distance to the material, according to one embodiment of the present disclosure. As in FIG. 1, the example apparatus 100 includes the laser device 130, the coupler 140, the laser catheter 170, and the at least one controller 180. The laser device 130 includes a light source to which the laser catheter 170 is coupled by way of the coupler 140. As shown in FIG. 5, the light source may take the form of a laser source 500 (e.g., an excimer laser, etc.) or a diagnostic light source 502 (e.g., an LED), where the laser source 500 is used for treatment (e.g., therapeutic purposes such as ablation). In another example, both the laser source 500 and the diagnostic light source 502 may be used at differing times as desired or as best suited to a particular application (e.g., a particular region of the vasculature under analysis).

The laser catheter 170 includes at least one fiber bundle 504, which in turn may include the at least one source fiber 300 configured to supply light from the light source to a region 506 within the vascular system of a patient so as to illuminate the region 506. The region 506 may comprise an electrical lead or leads as discussed above and, in some cases, buildup or deposit of unwanted material on or surrounding the lead(s). The at least one fiber bundle 504 may also include the at least one return fiber 302 configured to receive light reflected from the region 506 and the at least one additional fiber 304 to enable determination of the intensity of the light supplied by the source fiber(s) 300 from the light source. The at least one return fiber (e.g., return fibers 302a-302d) may, for example, be configured to receive the reflected light between pulses of laser light supplied from the light source via the source fiber(s) 300. In another embodiment, the at least one return fiber 302 may be configured to receive the reflected light from the region 506 within the vascular system of the patient where the light source is the diagnostic light source 502. The at least one return fiber 302 may provide the reflected light to the coupler 140, which may in turn provide the reflected light to the at least one controller 180 for analysis as described below.

In various vascular intervention procedures, particularly in lead removal procedures, it may be desirable to control the intensity of light supplied via the source fiber(s) 300 to the region 506 for each individual fiber; that is, on a fiber-by-fiber basis. For example, a typical electrical lead passes through a portion of the superior vena cava (SVC), and the SVC includes a relatively notable bend. In passing the laser catheter 170 through that bend during a lead removal procedure, it may be useful for a clinician to be able to control the amount of laser energy being emitted by the various fibers within the laser ablation catheter. That is, the intensities in individual ones of the source fibers 300 may be varied with respect to one another under control of the laser device 130. This may be done by the clinician or automatically by the device itself. For example, source fibers 300 interior to the bend in the SVC may not need an adjustment of the intensity of light passing therethrough from the light source, but source fibers 300 on the outside portion of the bend in the SVC may need a reduction in the intensity of source light passing therethrough.

Similarly, there may be situations in which a clinician wishes to control, or needs the ability to control, intensities of light supplied by different ones of the source fibers 300 based on the intensities of reflected light received by different ones of the return fibers 302 (which reflected light is discussed in further detail below) in order to avoid vascular tissue tearing and other dangerous or undesirable results.

Accordingly, in an embodiment of the present disclosure, intensities of light supplied by various ones of the source fibers 300 near a particular one of the return fibers 302 (e.g., return fiber 302*a*) may not be adjusted, while intensities of light supplied by various ones of the source fibers 300 near another particular one of the return fibers 302 (e.g., return fiber 302*c*) may be adjusted, such as when the intensity of reflected light received by the return fiber 302*c* meets particular conditions such as falling within a color-specific range or ranges of intensity, exceeding color-specific thresholds, etc.

Still further, in an embodiment of the present disclosure, the intensity/intensities of reflected light received by one or more of the return fibers 302 may be used to adjust the intensity/intensities of light supplied by various ones of the source fibers 300 within the laser catheter 170. As just several examples, the intensity of reflected light received by one return fiber (e.g., return fiber 302*a*) may be used to adjust the intensity of light supplied by source fibers 300 near the one return fiber, the intensity of light supplied by all source fibers 300, or the intensity of reflected light received by more than one of the return fibers 302 may be averaged or weighted in any other suitable manner and similarly used to adjust the intensity of light supplied by some or all of the source fibers 300. Any suitable use of the intensity/intensities of reflected light received by one or more of the return fiber(s) 302 to adjust the intensity of one or more of the source fiber(s) 300 may be implemented. Such suitable uses further include, by way of example, applications such as controlling therapeutic energy based on contacted tissue, e.g., increasing laser energy or selecting different laser types for ablating calcified plaque and decreasing energy for ablating soft plaque.

As shown in FIG. 5, the at least one controller 180 may include at least one processor 508 coupled to at least one memory 510 and input/output (I/O) device(s) 512. The I/O device(s) 512 may include one or more keys, touch screens or other displays, dials, lights, audio input or output devices, a mouse, and/or any other suitable I/O device(s). The at least one processor 508 may include laser device output logic 514 coupled to the laser device 130 and configured to control at least one of a pulse rate, a power level, and other characteristics of the optical energy output by the laser source 500 and/or the diagnostic light source 502. The at least one processor 508 may also include optical property sensing logic 515 configured to receive the output of the coupler 140, after the coupler 140 receives the reflected light from the at least one return fiber 302 (e.g., return fibers 302*a*-302*d*), and to generate signals indicative of sensed optical properties of the reflected light.

In one embodiment, the optical property sensing logic 515 may be implemented in hardware and may include, for example, at least one of a spectrometer, filtered light sensor(s), charge-coupled device (CCD) array with suitable optics and/or filters, etc. The at least one processor 508 may further include optical property determining logic 516 coupled to the optical property sensing logic 515, and the optical property determining logic 516 may be coupled to material type determining logic 518 and material distance determining logic 520 in order to determine a type of a material in the region 506 within the vascular system of the patient and in order to determine a distance to the material in the region 506, respectively.

Each of the laser device output logic 514 and other logic described herein may be implemented as software by executing suitable instructions on, for example, the at least one processor 508, or by storing executable instructions on a computer-readable medium (e.g., in the at least one memory 510), where the executable instructions are executable by at least one processor such as the at least one processor 508 to cause the at least one processor to perform the actions described herein. The various logic described herein may also be implemented in any other suitable manner, such as but not limited to a hardware implementation or any suitable combination of the example implementations described above. In the case of, for example, a hardware implementation, it will be appreciated from the disclosure herein that the various logic described may be physically distinct from the at least one processor 508. Additionally, in some cases, one or more of the logic elements described herein may be implemented as or considered as a single logic element, such as, for example, the optical property sensing logic 515 and the optical property determining logic 516. For example, the optical property sensing logic 515 and the optical property determining logic 516 may be implemented as or considered as a single logic element that senses optical properties of the reflected light, generates signals indicative of the sensed optical properties, and determines the optical properties based on the generated signals.

The reflected light received from the at least one return fiber 302 may be indicative of at least one of a transmittance, a reflectance, an absorbance, and a scattering coefficient of the region 506 within the vascular system of the patient. As understood by one skilled in the art, transmittance may be expressed as the percentage of incident light (electromagnetic radiation) on a sample (e.g., tissue in the patient's body) at a particular wavelength that is transmitted through the sample. Absorbance may be expressed as the percentage of incident light (electromagnetic radiation) on a sample at a particular wavelength that is absorbed by the sample. Reflectance may be expressed as the percentage of incident light (electromagnetic radiation) on a sample at a particular wavelength that is reflected by the sample. The reflected light received from the at least one return fiber 302 may also be indicative of at least one of a polarization of a tissue in the region 506 and optical coherence tomography data associated with the material in the region 506, and/or these and/or other suitable optical properties of the region 506 may be sampled and indicated by the output of the at least one return fiber 302 to the coupler 140.

The output of the coupler 140, which may be a modified coupler so as to couple both the at least one source fiber 300 and the at least one return fiber 302, and if desired the at least one additional fiber 304 as well, to the laser device 130 and/or the at least one controller 180, may be provided (e.g., as an image or video frame) to the optical property sensing logic 515 as described above. In another embodiment, a coupler separate from the coupler 140 (which separate coupler is not shown) may couple, for example, the at least one return fiber 302 and, in some cases, the at least one additional fiber 304 to, for example, the at least one controller 180.

The optical property sensing logic 515 may receive the output of the coupler 140 so as to generate at least one signal indicative of sensed optical property or properties of the reflected light. The at least one signal generated by the optical property sensing logic 515 may be provided to the optical property determining logic 516, which may determine at least one property (e.g., at least one optical property) of the region 506 based on the at least one signal provided by the optical property sensing logic 515. The at least one property of the region 506 may include at least one of a transmittance of the region 506, a reflectance of the region 506, an absorbance of the region 506, a scattering coefficient of the region 506, and an intensity of the reflected light within a spectrum. For example, the optical property sensing logic 515 and the optical property determining logic 516 may use changes in intensity of reflected light to determine the reflectance of the region 506. Other example ways of receiving the output of the coupler 140 so as to determine the at least one property of the region 506 will be understood by those of skill in the art after understanding the present disclosure.

The optical property determining logic 516 may send information regarding the determined at least one property of the region 506 to the material type determining logic 518. In some embodiments, the optical property determining logic 516 may also or alternatively send information regarding the determined at least one property to the material distance determining logic 520. The material type determining logic 518 may determine, based on the information from the optical property determining logic 516, the type of the material in the region 506. As just one example, the material type determining logic 518 may analyze the determined at least one property of the region 506 within the vascular system by analyzing diffuse absorbance and transmittance (DAAT) characteristics of the region 506 as determined by the optical property determining logic 516 to determine that the type of the material in the region 506 comprises biological material and, more particularly, that the type of the material comprises one of blood or tissue.

In other embodiments, the analysis by the material type determining logic 518 may further indicate that the type of the material in the region is biological material, for example, a particular cell type or biomolecule associated with the cells of a particular tissue, such as SVC tissue, which may be particularly useful in assisting a clinician in avoiding dangerous SVC tears when performing ablation using the laser catheter 170. In still further examples, the material type determining logic 518 may determine that the type of the material in the region 506 comprises non-biological material, such as, for example, fat deposits (e.g., cholesterol monohydrate, cholesterol esters and phospholipids), fibrous tissue (e.g., fibrin, proteoglycans, collagen), calcium deposits (e.g., calcium oxide, calcium carbonate, calcium phosphates), and remnants of dead cells and cellular debris in the region 506, etc.

As discussed above, the optical property determining logic 516 may also or alternatively send the information regarding the determined at least one property of the region 506 within the vascular system of the patient to the material distance determining logic 520. The material distance determining logic 520 may determine, based on the information from the optical property determining logic 516, an indication of a distance to the material in the region 506 within the vascular system. For example, the material distance determining logic 520 may cause the at least one controller 180 to generate an indication (e.g., via the I/O device(s) 512) that the distance to the material in the region 506 is shorter than desired based on the determined type of the material in the region (e.g., based on determining that the type of the material in the region 506 is SVC tissue, the at least one controller 180 may generate an indication of a risk of causing an SVC tear given the distance to the SVC). The material distance determining logic 520, and/or the material type determining logic 518, may also determine whether the material in the region 506 is a proper target for laser ablation (e.g., based on the type of the material in the region 506 and/or the distance to the material in the region 506). For example, if the material distance determining logic 520 indicates that the laser catheter 170 is in dangerously close contact with the SVC, the material distance determining logic 520 may determine that the material in the region 506 is not a proper target for ablation.

The material type determining logic 518 and the material distance determining logic 520 may also or alternatively be configured to cause the at least one controller 180 to generate, such as via the I/O device(s) 512, an alert based on the determined type of the material in the region 506 and/or the determined distance to the material. The alert may, for example, prompt a clinician to adjust an intensity of, or power off, the light source (e.g., laser source 500 or diagnostic light source 502).

In accordance with an embodiment of the present disclosure, the material type determining logic 518 and/or the material distance determining logic 520 may analyze the information from the optical property determining logic 516 (e.g., determined transmittance, reflectance, absorbance, and/or scattering coefficient of the region 506) with respect to a library of information regarding different types of materials and/or distances to materials in order to determine material type and/or indication of distance, respectively. The library of information may, in one embodiment, be contained within the at least one memory 510, and may comprise any suitable executable instructions or other content within memory to allow the material type determining logic 518 and/or the material distance determining logic 520 to determine material type in the region 506 and/or indication of distance to the material in the region 506. The information from the optical property determining logic 516 regarding the determined at least one property of the region 506 may, for example, be compared against information in the library to determine the type of the material in the region 506 and/or the distance to the material.

Furthermore, in accordance with an embodiment of the present disclosure, the optical property determining logic 516 may receive the output of the coupler 140 so as to determine at least one property of the region 506 on a fiber-by-fiber basis. That is, the optical property determining logic 516 may determine the at least one property individually for each of the return fibers 302, thus allowing the determining of the type of the material in the region 506 and/or the indication of the distance to the material in the region 506 to be performed/provided for each individual one of the fibers 302. Such individualized determinations may be useful when, for example, the laser catheter 170 is contacting blood or tissue at an angle and thus the characteristics of reflected light at each of the return fibers 302 are different (see, e.g., discussion of FIG. 7B below). Additionally, the I/O device(s) 512 may, for example, display per-fiber feedback in real time and/or in a visual arrangement that corresponds to the geometric arrangement of the fibers at the tip of the laser catheter 170. In one embodiment, real-time visualizations may be displayed, on a per-fiber basis if desired, by overlaying the real-time visualizations onto existing fluoroscopy displays.

FIGS. 6A, 6B, 7A, and 7B are simplified views of reflected diffuse absorbance and transmittance (DAAT) characteristics from the perspective of, for example, a clinician viewing the outputs of the return fibers 302, as understood by one skilled in the art in view of the present disclosure, based on the laser catheter 170 being in regions with different types of materials and being at different distances (including different angles) to such types of materials. In particular, FIG. 6A illustrates a view 600 of reflected DAAT characteristics as viewed from the outputs of return fibers 302a-302d when a catheter tip, such as a tip of the laser catheter 170, is in an approximately ten millimeter (mm) deep pool of blood. FIG. 6B illustrates the slightly more visible reflected DAAT characteristics, as indicated by cross-hatched lines not present in FIG. 6A, when the catheter tip is in a shallower (e.g., approximately four mm) deep pool of blood. FIG. 7A illustrates the increasingly visible reflected DAAT characteristics, as indicated by solid lines not present in either of FIG. 6A or 6B, when the catheter tip is in full (e.g., normal) contact with tissue. FIG. 7B illustrates a relatively mixed visibility of reflected DAAT characteristics that may be present when, for example, the catheter tip is in contact with planar tissue at an angle (e.g., an approximately 15 degree angle).

Figure 8:
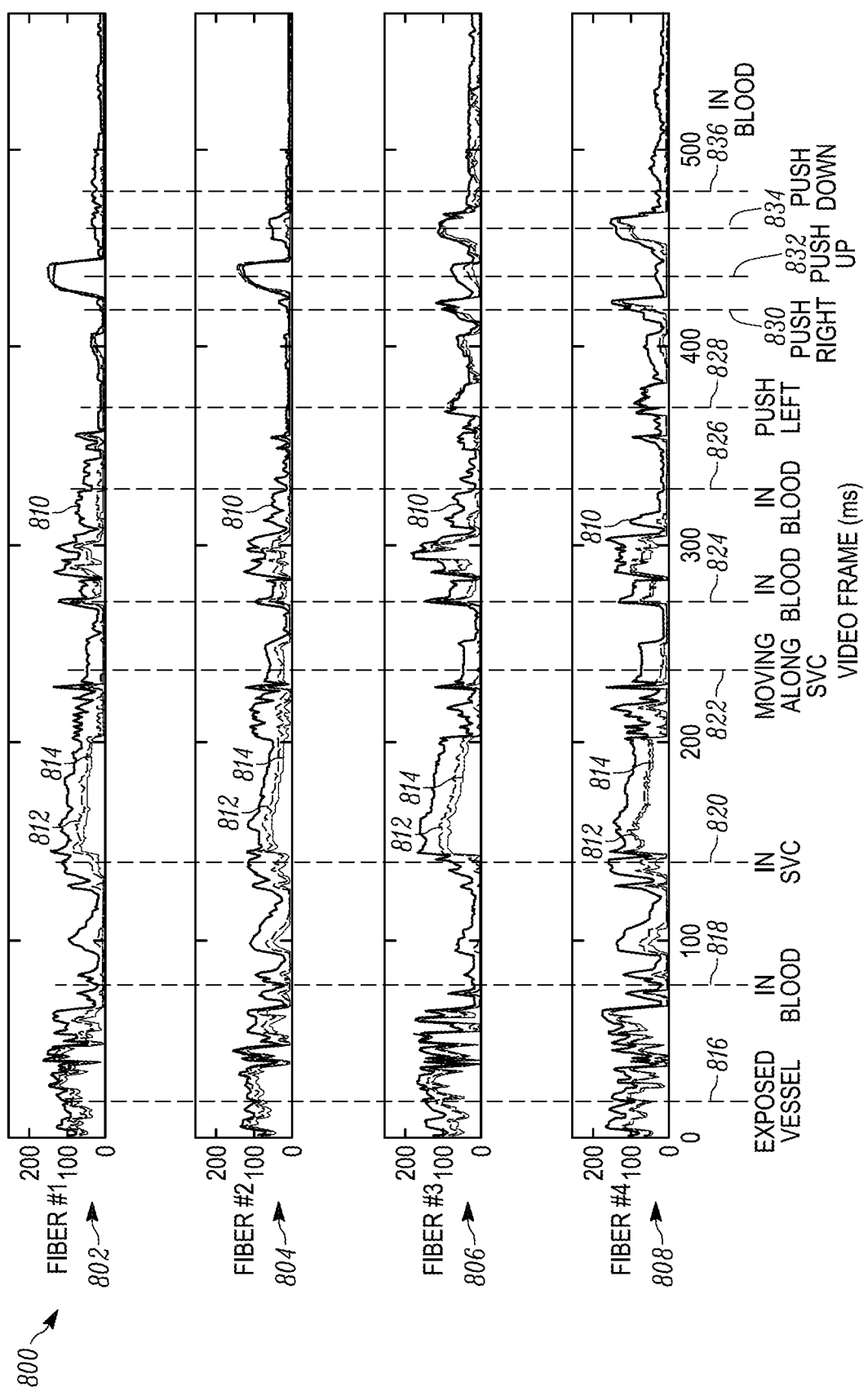
FIG. 8 illustrates a group of video frames of each of four return fibers, including example intensities of a red channel, a green channel, and a blue channel for each of the return fibers and example corresponding indications of type of a material and/or distance to a material in a region within a vascular system of a patient.

Turning now to FIG. 8, as noted above with respect to FIG. 5, the optical property determining logic 516 may determine at least one property of the region 506 from the reflected light from the region 506, and the at least one property may include an intensity of the reflected light within a spectrum. In particular, as discussed above, the optical property determining logic 516 may use changes in intensity of reflected light to determine the reflectance of the region 506. In one embodiment, the optical property determining logic 516 may apply pixel masks to image or video frames corresponding to each of the return fibers 302 in order to separate out red, green, and blue channel intensity values associated with the reflected light for each return fiber 302, thereby analyzing the reflected light from the region 506 to determine the intensity values. FIG. 8 illustrates a group 800 of video frames of each of four return fibers 802, 804, 806, and 808, which may be the return fibers 302*a*-302*d* previously discussed herein.

More specifically, the group 800 of video frames shows example intensities of a red channel 810, a green channel 812, and a blue channel 814 for each of the return fibers 802, 804, 806, and 808 and example corresponding indications of type of a material and/or distance to a material. For example, along the horizontal (time) axis, indication 816 shows that a catheter tip (e.g., a tip of laser catheter 170) is contacting an exposed vessel within the vascular system of a patient. Indication 818 shows that the catheter tip is in blood; indication 820 shows that the catheter tip is in the SVC; indication 822 shows that the catheter tip is moving along the SVC; indications 824 and 826 show that the catheter tip is in blood; indication 828 may alert a clinician to move or push the catheter to the left; indication 830 may alert the clinician to move or push the catheter to the right; indication 832 may alert the clinician to move or push the catheter up; indication 834 may alert the clinician to move or push the catheter down; and indication 836 may alert the clinician that the catheter tip is in blood. It will be appreciated upon review of the present disclosure that the waveforms of intensities of the red, green, and blue channels 810, 812, and 814, and the corresponding indicators 816-836, are not necessarily indicative of the conditions that may exist in a particular application, as such intensities and conditions may depend upon a number of factors such as characteristics of the catheter employed, fiber characteristics, etc.

FIGS. 8A-8C illustrate several magnified views of different portions of the video frame for one of the four return fibers of FIG. 8, specifically in this example the return fiber 808. The magnified views include magnified views of the example intensities shown in FIG. 8 of the red channel 810, the green channel 812, and the blue channel 814 for the return fiber 808 and several of the corresponding indications shown in FIG. 8. In particular, in the example of FIG. 8A, a magnified view is shown of the portion of the video frame for the return fiber 808 near the indication 818 that the catheter tip is in blood. As shown in FIG. 8A, the intensity of the red channel 810 may, for example, be greater than the intensities of both the green channel 812 and the blue channel 814. In the example of FIG. 8B, a magnified view is shown of the portion of the video frame for the return fiber 808 near the indication 820 that the catheter tip is in the SVC. In the example of FIG. 8C, a magnified view is shown of the portion of the video frame for the return fiber 808 near the indication 822 that the catheter tip is moving along the SVC. As shown in FIGS. 8A and 8B, the intensities of the red, green, and blue channels may, for example, each be higher when the catheter tip is in the SVC, as shown in FIG. 8B, as compared to when the catheter tip is in blood, as shown in FIG. 8A. Additionally, as shown in FIGS. 8B and 8C, the intensities of the red, green, and blue channels may, for example, each be higher when the catheter tip is in the SVC as compared to when the catheter tip is moving along the SVC. Furthermore, the intensities of the green channel 812 and the blue channel 814 may, for example, be notably lower when the catheter tip is moving along the SVC, both compared to the intensity of the red channel 810, when the catheter tip is moving along the SVC and compared to the intensities of the green and blue channels when the catheter tip is in the SVC.

Figure 9:
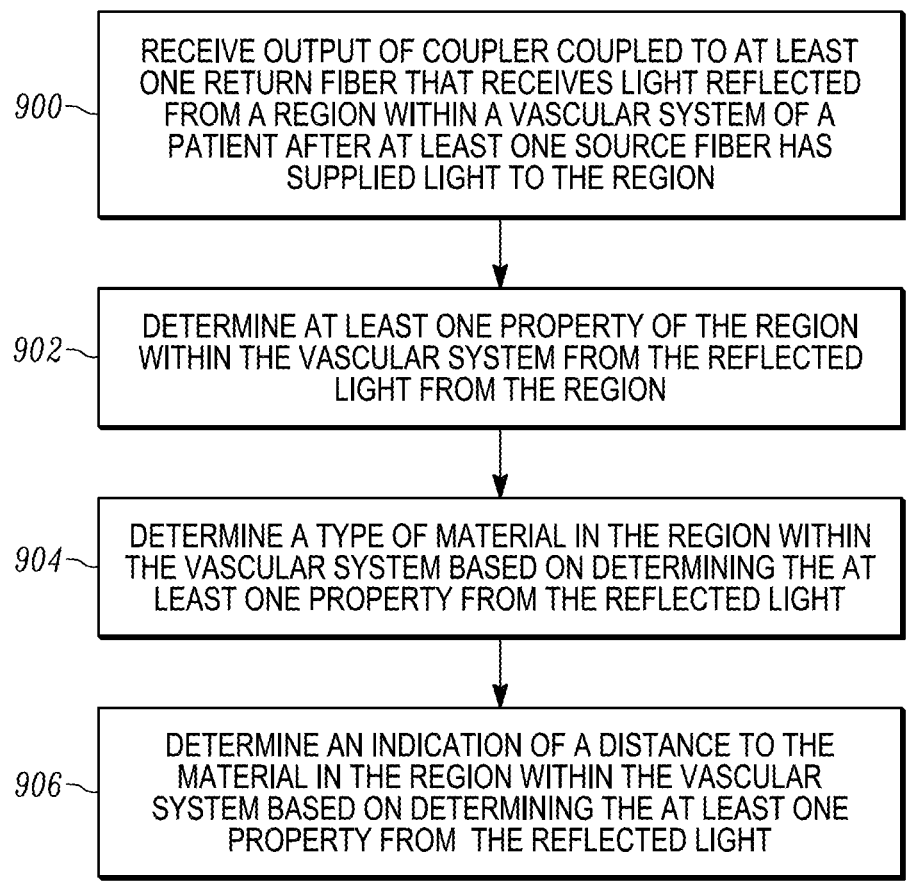
FIG. 9 is a flowchart of an example method for determining a type of a material in a region in a vascular system of a patient.

FIG. 9 is a flowchart of an example method for determining a type of a material and an indication of a distance to the material in a region in a vascular system of a patient. Each of the method illustrated in FIG. 9 and the method illustrated further below in FIG. 10 may be carried out by one or more suitably programmed controllers or processors executing software (e.g., by the at least one controller 180). Each of the methods may also be embodied in hardware or a combination of hardware and hardware executing software. Suitable hardware may include one or more application specific integrated circuits (ASICs), state machines, field programmable gate arrays (FPGAs), digital signal processors (DSPs), and/or other suitable hardware. Although the methods are described with reference to the illustrated flowcharts, it will be appreciated that many other ways of performing the acts associated with the methods may be used. For example, the order of some operations may be changed, and some of the operations described may be optional. Additionally, while the methods may be described with reference to the example apparatus 100, it will be appreciated that the methods may be implemented by other apparatus as well, and that the apparatus 100 may implement other suitable methods.

As to FIG. 9, as shown in block 900, the method may include receiving an output of a coupler (e.g., receiving, by the at least one controller 180, an output of the coupler 140) coupled to at least one return fiber (e.g., 302) that receives light reflected from a region (e.g., 506) within a vascular system of a patient after at least one source fiber (e.g., 300) has supplied light to the region.

As shown in block 902, the method may also include determining (e.g., by the optical property determining logic 516) at least one property of the region within the vascular system from the reflected light from the region.

As shown in block 904, the method may also include determining (e.g., by the material type determining logic 518) a type of a material in the region within the vascular system based on determining the at least one property from the reflected light.

As shown in block 906, the method may also include determining (e.g., by the material distance determining logic 520) an indication of a distance to the material in the region within the vascular system based on determining the at least one property from the reflected light. The method may then end and may be repeated as needed or desired.

Figure 10:
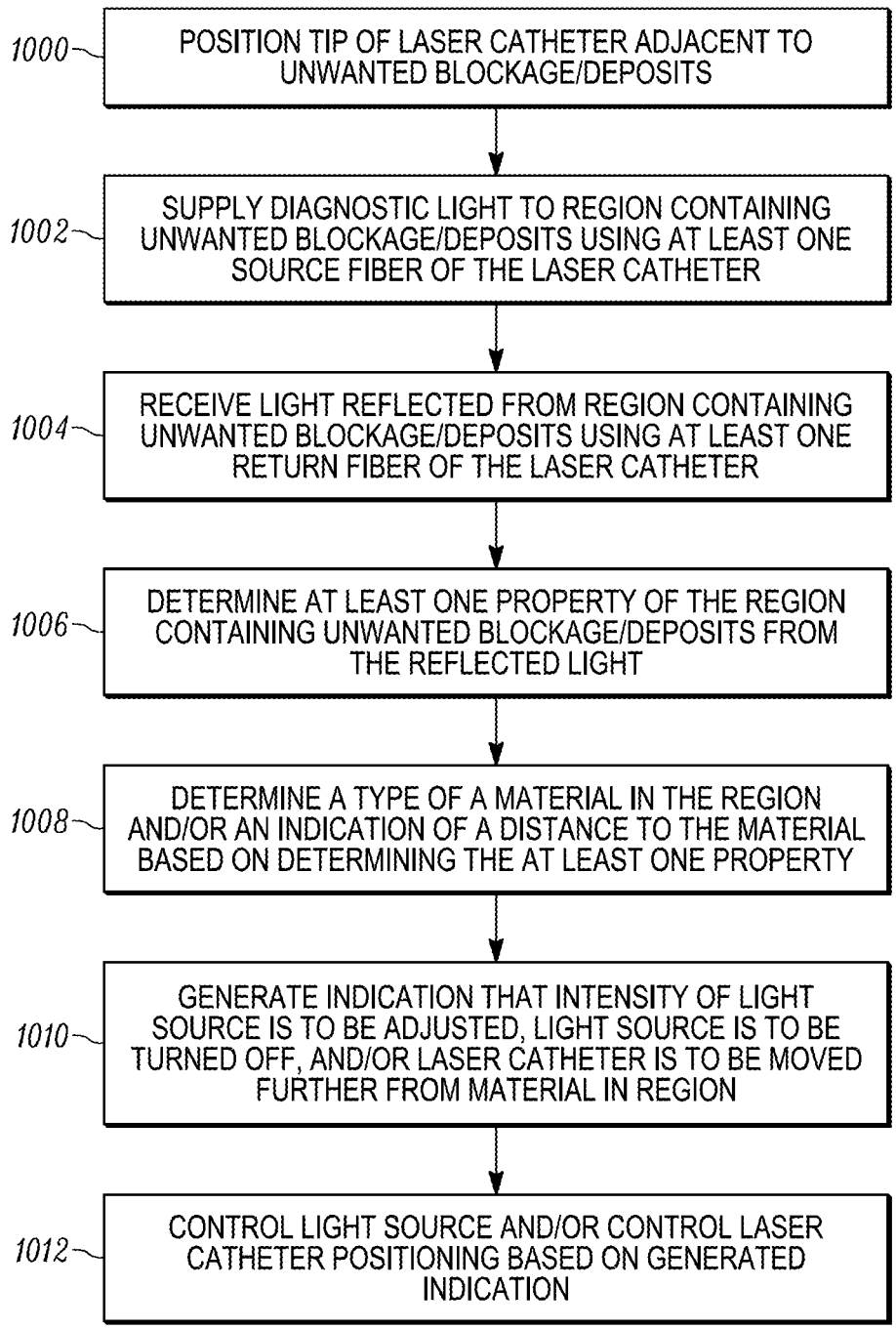
FIG. 10 is a flowchart depicting the steps of a surgical procedure using an embodiment of the laser catheter of the present disclosure.

FIG. 10 is a flowchart of an example method for determining a type of a material and an indication of a distance to the material in a region in a vascular system of a patient, and for controlling a light source and/or controlling laser catheter positioning accordingly. As shown in block 1000, the method may include positioning a tip of a laser catheter (e.g., 170) adjacent to unwanted blockage and/or deposits, such as those surrounding an electrical lead or those in, for example, a peripheral artery.

As shown in block 1002, the method may also include supplying diagnostic light to a region (e.g., 506) containing the unwanted blockage/deposits using at least one source fiber (e.g., 300) of the laser catheter.

As shown in block 1004, the method may include receiving light reflected from the region containing unwanted blockage/deposits using at least one return fiber (e.g., 302) of the laser catheter 170.

As shown in block 1006, the method may also include determining at least one property (e.g., by the optical property sensing logic 515 receiving the output of the coupler 140 and generating at least one signal indicative of a sensed property of the reflected light, and by the optical property determining logic 516 determining the at least one property based on the signal generated by the optical property sensing logic 515) of the region containing the unwanted blockage/deposits from the reflected light.

As shown in block 1008, the method may include determining a type of a material in the region and/or an indication of a distance to the material in the region (e.g., by the material type determining logic 518 and/or the material distance determining logic 520) based on determining the at least one property of the region.

As shown in block 1010, the method may also include generating an indication (e.g., by the I/O device(s) 512) that an intensity of the light source is to be adjusted, that the light source is to be turned off, and/or that the laser catheter is to be moved further from the material in the region. Alternatively, an indication may be generated that the laser catheter is to be moved closer to the material in the region. The indication may be generated based on the determination(s) made in block 1008.

As shown in block 1012, the method may also include controlling the light source and/or controlling the positioning of the laser catheter 170 based on the generated indication (e.g., block 1010). The method may then end and may be repeated as needed or desired.

Figure 11:
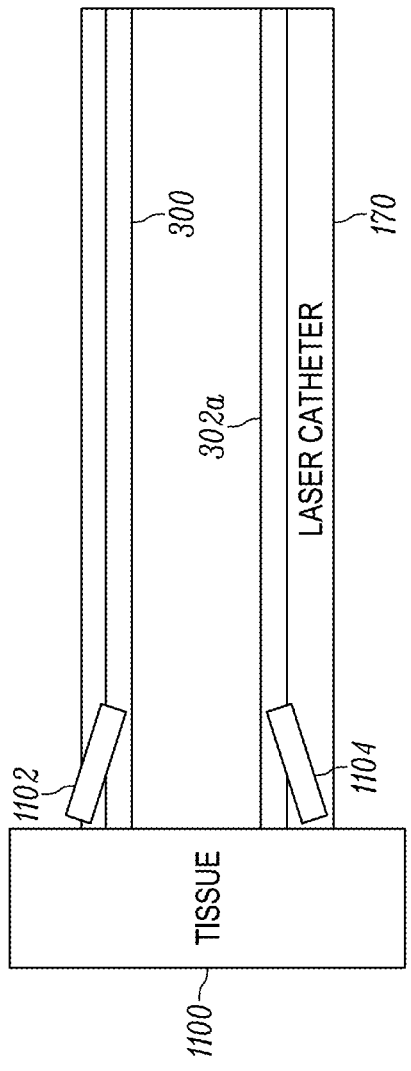
FIG. 11 illustrates an example use of displacement of source and/or return fibers to treat a broader area within a vascular system of a patient.

FIG. 11 illustrates an example of displacement of source and/or return fibers to treat a broader area within a vascular system of a patient, such as to treat a broader area within the region 506, as compared to when such displacement of source and/or return fibers is not implemented. As shown in FIG. 11, the laser catheter 170 may, for example, be in contact with a portion of tissue 1100. One of the source fibers 300 and one return fiber, in this example the return fiber 302a, is also shown within the laser catheter 170. As shown in the example of FIG. 11, one or both of an end portion 1102 of the source fiber 300 and an end portion 1104 of the return fiber 302a may be capable of being displaced at any suitable time during illumination via the source fiber 300 and/or collection of light via the return fiber 302a. Such displacement may allow information to be gathered, by way of the reflected light as discussed above, from a broader (e.g., more expansive) area within the region 506 (e.g., from more of the portion of the tissue 1100), and/or may allow treatment of a broader area within the region 506 as compared to when such displacement is not used. The displacement of the end portion 1102 and/or the end portion 1104 may be implemented in any suitable manner, such as but not limited to actuation by resonant vibrations or static displacements via piezo-electric or laser-induced thermal actuation. Additionally, it will be understood that the illustration in FIG. 11 is one example implementation of displacement of, for example, the source fiber 300 and/or the return fiber 302a, and that other suitable ways of implementing such displacement may also be employed.

Figure 12:
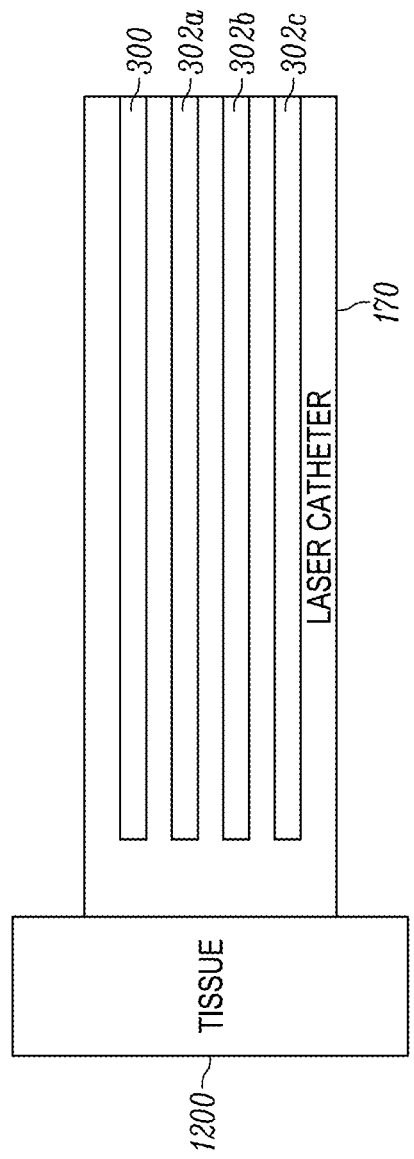
FIG. 12 illustrates an example use of an offset between ends of source and/or return fibers and a tip of a laser catheter to facilitate determination of properties of reflected light.

FIG. 12 illustrates an example of an offset between ends of source and/or return fibers and a tip of a laser catheter to facilitate determination of properties of the reflected light. As shown in FIG. 12, the laser catheter 170 may, for example, be in contact with another example portion of tissue 1200. One of the source fibers 300 and several return fibers, such as the return fibers 302a, 302b, and 302c are shown within the laser catheter 170 in FIG. 12. The ends of the source fiber 300 and the return fibers 302a-302c may be offset from the point (e.g., surface) at which the laser catheter 170 is in contact with the portion of the tissue 1200. Any suitable offsets may be used, and some offsets may be the same, as in the case of the return fibers 302a-302c in the example of FIG. 12. Additionally, if desired, one or more fibers may not be offset. The use of offsets may facilitate more accurate diffuse reflection measurements, which may, for example, result in more accurate reflected DAAT characteristics as discussed above with respect to, for example, FIGS. 6A, 6B, 7A, and 7B.

Figure 13:
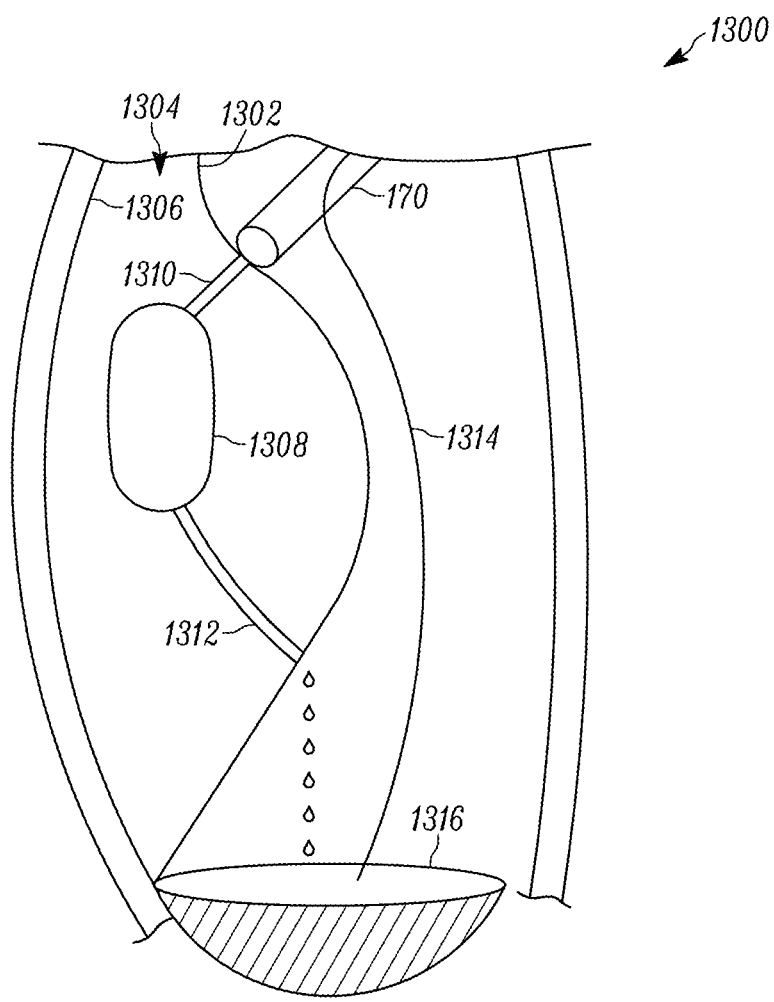
FIG. 13 illustrates an example portion of a human vasculature, such as an example portion of a blood vessel.

FIG. 13 illustrates an example portion of a human vasculature, such as an example portion 1300 of a blood vessel. The portion 1300 of the blood vessel may include an endothelial cell layer 1302 and a buildup (or deposit) 1304, which may be or may include plaque, between the endothelial cell layer 1302 and a vessel wall 1306. It will be understood from the present disclosure that in various embodiments, the portion 1300 of the blood vessel shown in FIG. 13 may be, may include, or may be included within the region 506 of the vascular system as discussed above. The buildup 1304 includes a fatty core 1308. It may be necessary or desirable to ablate the fatty core 1308, which may be or may contain hardened plaque, without ablating other portions of the buildup 1304. By removing (e.g., ablating) the fatty core 1308 without removing other portions of the buildup 1304, more living layers of tissue may be spared from lasing, which may lessen inflammatory and immune responses. As a result, the risk of restenosis may advantageously be reduced.

Through the use of techniques such as those described above to determine a type of a material in a region within the vascular system, and an indication of a distance to such material, selective ablation of the fatty core 1308 may be achieved. Based on a determined type of a material and/or indication of distance to such material, the buildup 1304 and the fatty core 1308 may be identified and the at least one source fiber 300 may ablate a portion of the buildup 1304 so as to create an entry path 1310 into the fatty core 1308. Lasing may then cause the fatty core 1308 to ablate, and the resulting ablated plaque may pass through an exit path 1312. A guidewire 1314 may hold the laser catheter 170 in a position so as to perform the ablation and so that the ablated plaque that passes through the exit path 1312 is collected with a downstream occlusion filter 1316 that ensures, for example, that the ablated plaque does not mix into the bloodstream of the patient.

Figure 13A:
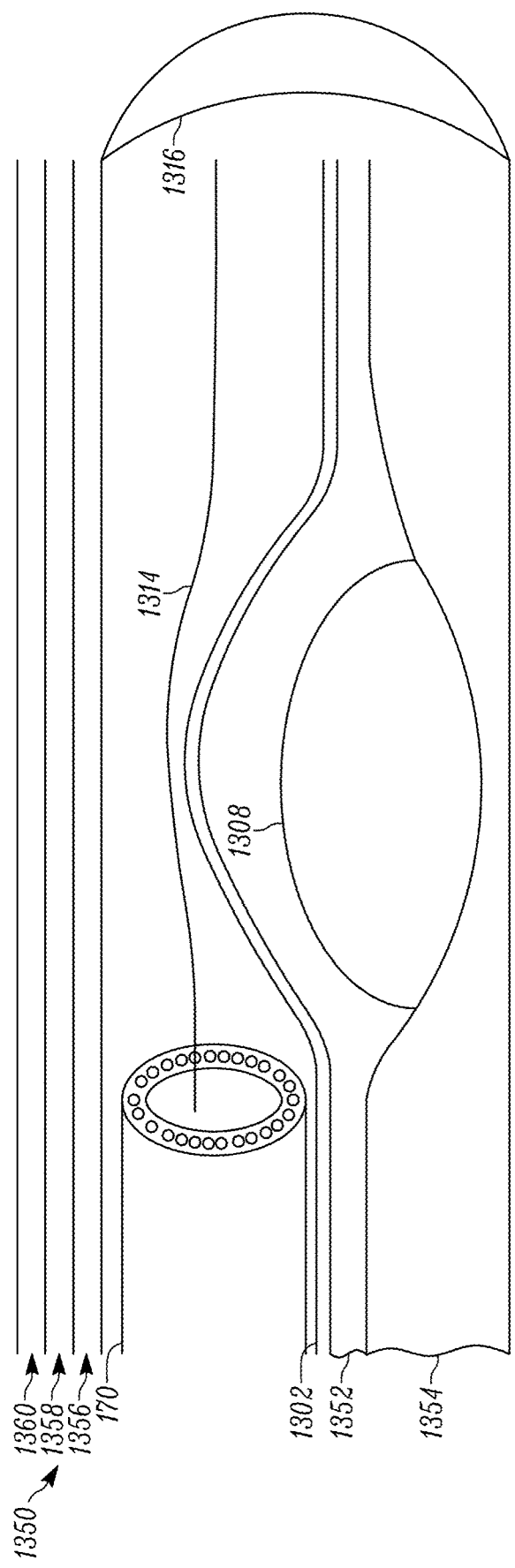
FIGS. 13A-13C illustrate an example portion of a human vasculature, such as an example portion of a blood vessel, with examples of positioning and/or use of a laser catheter for ablation.
Figure 13B:
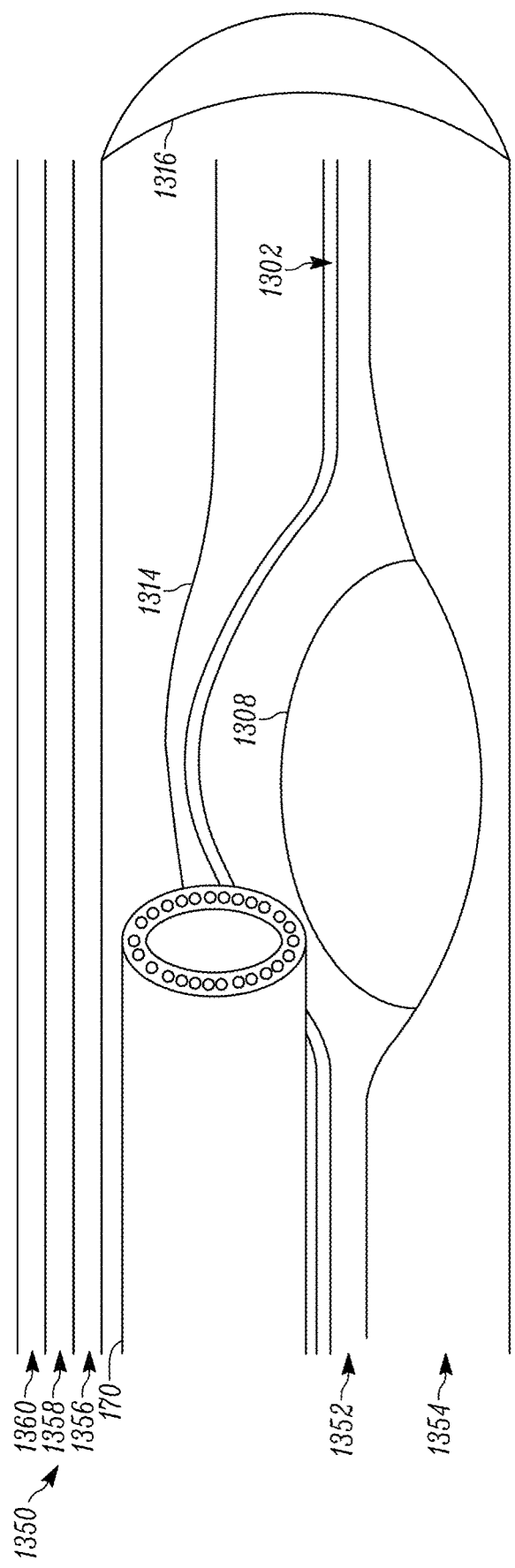
Figure 13C:
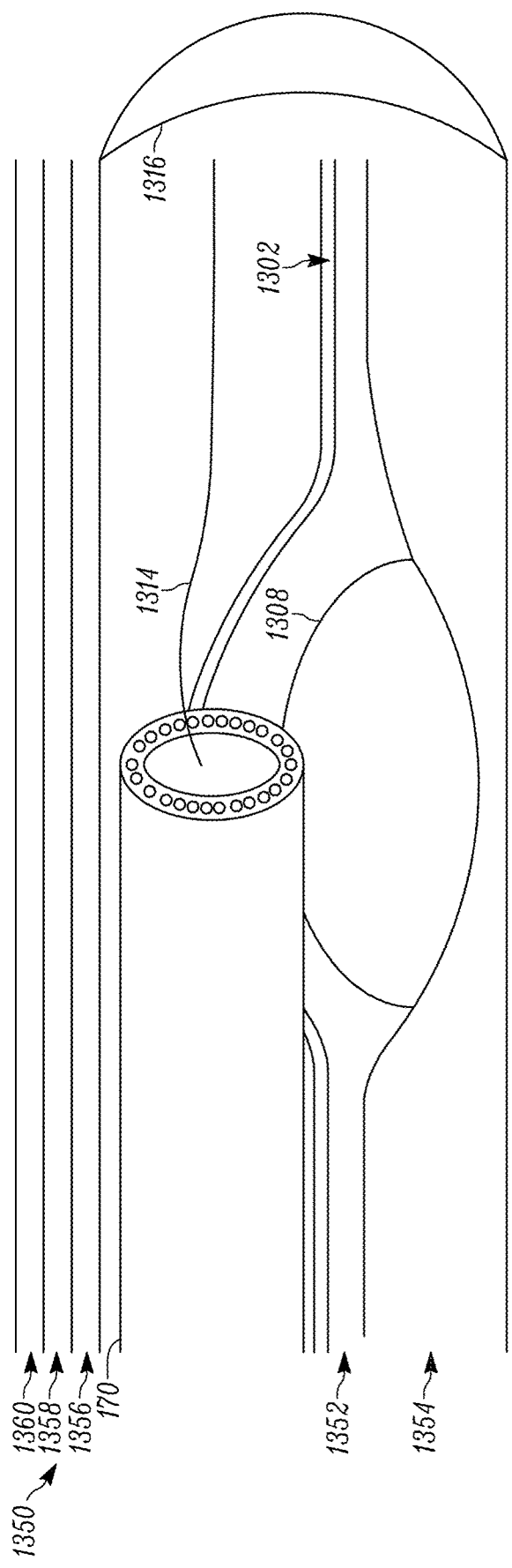

FIGS. 13A-13C illustrate an example portion of a human vasculature, such as an example portion 1350 of a blood vessel, with examples of positioning and/or use of a laser catheter for ablation. It will be understood from the present disclosure that in various embodiments, the portion 1350 of the blood vessel may be, may include, or may be included within the region 506 of the vascular system as discussed above. For example, FIG. 13A shows that the example portion 1350 may include a portion of the endothelium 1302 in vasculature, a portion of the intima 1352 in vasculature, and a portion of the media 1354 in vasculature. A buildup including the fatty core (e.g., containing hardened plaque) 1308 is shown in the intima 1352. The guidewire 1314 may position the laser catheter 170 in preparation for ablation, with the downstream occlusion filter 1316 positioned to collect ablated material in order to ensure that, for example, the ablated material does not mix into the bloodstream of the patient. The endothelium 1356, the intima 1358, and the media 1360 on an opposite wall of the portion 1300 of the blood vessel are also illustrated for completeness.

As shown in FIG. 13B, the laser catheter 170 may be advanced, using, e.g., the guidewire 1314, into the intima 1352 so that the laser catheter 170 is adjacent the fatty core 1308. As shown in FIG. 13C, the laser catheter 170 may be further advanced into the fatty core 1308 for ablation of the fatty core. By removing (e.g., ablating) the fatty core 1308 without removing other portions of the intima 1352, more living layers of tissue may be spared from lasing, which may lessen inflammatory and immune responses. In particular, through the use of techniques such as those described above to determine a type of a material in a region within the vascular system, and an indication of a distance to such material, selective ablation of the fatty core 1308 may be achieved. As a result, the risk of restenosis may advantageously be reduced.

It will be appreciated that various modifications of the embodiments herein may be made after review of and understanding of the present disclosure. For example, different fiber tip geometries may be used to change the treatment and/or diagnostic areas as desired, and/or to control the gathering of reflected light. Diagnostic light source intensity may also be varied to more accurately reveal geometric features of tissues in some cases. Fluorescence and/or mitochondrial markers may be employed to discriminate tissue types, such as using mitochondrial markers to distinguish between live tissue and scar tissue. Force/strain measurements may be made using a diffraction grating (e.g., a Bragg diffraction grating) along the laser catheter 170 or its tip, or using interferometry-based microelectromechanical systems (MEMS) sensors. Force sensors may also be used to infer or determine tissue type, including whether tissue is comprised of biological material or non-biological material.

It will be further appreciated upon review of the disclosure that the example features and methods described herein thus allow ablation of unwanted blockage, deposits, etc. in a peripheral artery or, in a similar procedure, surrounding an electrical lead. In the case of an electrical lead, the lead itself may then be removed.

A number of variations and modifications of the disclosure can be used. It would be possible to provide for some features of the disclosure without providing others. Furthermore, embodiments of systems and methods according to the present disclosure may include and/or be used in conjunction with any of the systems, devices, structures, and/or methods described in U.S. patent application Ser. Nos. 13/800,651, 13/800,675, 13/800,700, and/or 13/800,728, all of which were filed on Mar. 13, 2013, the disclosures of which are hereby incorporated by reference in their entireties.

The present disclosure, in various aspects, embodiments, and configurations, includes components, methods, processes, systems and/or apparatus substantially as depicted and described herein, including various aspects, embodiments, configurations, sub-combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An apparatus for determining a type of a material in a region within a vascular system of a patient, the apparatus comprising:
a laser catheter coupled to a light source, the laser catheter comprising:
a distal end and a tip at the distal end;
at least one source fiber disposed at the tip and configured to supply light from the light source to a contact region within a vascular system of a patient so as to illuminate the contact region within the vascular system of the patient; and
at least one return fiber disposed at the tip and configured to receive light reflected from the contact region within the vascular system of the patient, the reflected light being indicative of diffuse absorbance and transmittance characteristics of the contact region within the vascular system of the patient; and at least one controller comprising a processor executing:

optical property determining logic configured to separate the reflected light into a plurality of channels, determine an intensity value for each plurality of channels and determine the diffuse absorbance and transmittance characteristics of the contact region within the vascular system of the patient, wherein the optical property determining logic identifies a change in intensity value for each plurality of channels and creates a waveform for each plurality of channels, wherein each waveform is representative of the intensity value over time; and material type determining logic configured to determine a type of a material in the contact region within the vascular system based on receiving the change in intensity value for each plurality of channels from the optical property determining logic, wherein the material type determining logic determines whether the contact region is blood or tissue.

2. The apparatus of claim 1, wherein the material type determining logic is further configured to analyze the determined diffuse absorbance and transmittance characteristics with respect to a library of information regarding different types of materials so as to determine the type of the material in the contact region within the vascular system.

3. The apparatus of claim 1, wherein the material type determining logic is further configured to determine, if the material type determining logic determines the contact region is tissue, a particular cell type for the tissue.

4. The apparatus of claim 1, wherein the material type determining logic is further configured to determine that the type of the material in the contact region within the vascular system comprises non-biological material.

5. The apparatus of claim 4, wherein the material type determining logic is further configured to determine that the non-biological material in the contact region within the vascular system comprises at least one of plaque or calcified tissue based on the diffuse absorbance and transmittance characteristics.

6. The apparatus of claim 1, wherein the reflected light is further indicative of at least one of a polarization of tissue in the contact region within the vascular system of the patient and optical coherence tomography data associated with the material in the contact region within the vascular system of the patient.

7. The apparatus of claim 1, wherein the laser catheter further comprises at least one additional fiber coupled to the light source, and wherein the processor having at least an optical determining logic is further configured to use received information from the at least one additional fiber to determine an intensity of the light supplied by the at least one source fiber from the light source.

8. The apparatus of claim 1, wherein the optical property determining logic is further configured to generate an indication that an intensity of a light source used for treatment in the contact region within the vascular system of the patient is to be adjusted or that the light source used for treatment is to be powered off based on the diffuse absorbance and transmittance characteristics, and wherein the light source used for treatment in the contact region is one of the light source used to supply light to the contact region for determining the type of the material in the contact region and a different light source.

9. An apparatus for determining a type of a material in a region within a vascular system of a patient and a distance to the material, the apparatus comprising:

a laser catheter coupled to a light source, the laser catheter comprising:

a distal end and a tip at the distal end;

at least one source fiber disposed at the tip and configured to supply light from the light source to a contact region within a vascular system of a patient so as to illuminate the contact region within the vascular system of the patient; and at least one return fiber disposed at the tip and configured to receive light reflected from the contact region within the vascular system of the patient, wherein the reflected light is indicative of diffuse absorbance and transmittance characteristics of the contact region; and at least one controller comprising a processor executing:

optical property determining logic configured to separate the reflected light into a plurality of channels, determine an intensity value for each plurality of channels and determine at least one property of the contact region within the vascular system from the reflected light from the contact region within the vascular system, wherein the optical property determining logic identifies a change in intensity value for each plurality of channels and creates a waveform for each plurality of channels, wherein each waveform is representative of the intensity value over time;

material type determining logic configured to determine a type of a material in the contact region within the vascular system based on receiving the change in intensity value for each plurality of channels from the reflected light based upon the optical property determining logic, wherein the material type determining logic determines whether the contact region is blood or tissue; and distance determining logic configured to determine an indication of a distance to the material in the contact region within the vascular system based on determining the at least one property from the reflected light based upon the optical property determining logic.

10. The apparatus of claim 9, wherein the material type determining logic is further configured to determine, if the material type determining logic determines the contact region is tissue, a particular cell type of the tissue, and wherein the material type determining logic is further configured to determine whether the contact region comprises non-biological material.

11. The apparatus of claim 10, wherein the processor is further configured to generate an alert associated with use of a light source for treatment in the contact region within the vascular system of the patient based on the material type determining logic, wherein the light source used for treatment in the contact region is one of the light source used to supply light to the contact region and a different light source.

12. The apparatus of claim 9, wherein the material type determining logic determines the type of the material in the contact region based in part on a geometry at a tip of the at least one return fiber receiving the reflected light.

13. The apparatus of claim 9, wherein the processor is further configured to determine, based on the material type determining logic, whether the material in the contact region within the vascular system is a proper target for laser ablation.

14. The apparatus of claim 9, wherein the processor is further configured to determine an indication of a distance to a boundary of the material in the contact region based on the distance determining logic.

15. A non-transitory computer-readable medium comprising executable instructions that when executed by one or more processors cause the one or more processors to:
- separate reflected light received from at least one return fiber disposed at the tip of a laser catheter and into a plurality of channels and determines an intensity value for each plurality of channels separate the reflected light into a plurality of channels, based on the at least one signal, wherein the reflected light is from a contact region within a vascular system of a patient after illumination of the contact region with light from a light source, wherein the reflected light is indicative of diffuse absorbance and transmittance characteristics of the contact region;
- determine an intensity value for each plurality of channels;
- determine a change in intensity value for each plurality of channels;
- create a waveform for each plurality of channels, wherein each waveform is representative of the intensity value over time;
- generate, based on the waveform, at least one signal indicative of at least one property of the contact region within the vascular system;
- determine the at least one property of the contact region within the vascular system, based on the waveform; and
- determine a type of a material in the contact region within the vascular system based on determining the at least one property of the contact region, wherein the executable instructions when executed by one or more of the processors cause the one or more processors to determine whether the contact region is blood or tissue.

16. The non-transitory computer-readable medium of claim 15, further comprising executable instructions that when executed by the one or more processors cause the one or more processors to determine, if the contact region is blood, an indication of a depth of the blood based on determining the at least one property of the contact region within the vascular system.

17. The non-transitory computer-readable medium of claim 15, further comprising executable instructions that when executed by the one or more processors cause the one or more processors to generate, based on determining the at least one property of the contact region within the vascular system, at least one of: (i) an indication that an intensity of the light source is to be adjusted, (ii) an indication that the light source is to be turned off, (iii) an indication that a laser catheter comprising source fibers used for the illumination of the contact region within the vascular system and at least one return fiber used to receive the reflected light is to be moved further from the material in the contact region within the vascular system, and (iv) an indication that the laser catheter is to be moved closer to the material in the contact region within the vascular system.

\* \* \* \* \*